United States Patent
Kang et al.

(10) Patent No.: US 8,634,701 B2
(45) Date of Patent: Jan. 21, 2014

(54) DIGITAL DATA REPRODUCING APPARATUS AND CORRESPONDING METHOD FOR REPRODUCING CONTENT BASED ON USER CHARACTERISTICS

(75) Inventors: Mingoo Kang, Seoul (KR); Haengjoon Kang, Seoul (KR); Jongsoon Park, Seoul (KR); Jinyung Park, Seoul (KR); Jongcheol Kim, Seoul (KR); Junho Park, Seoul (KR); Sunjung Hwang, Seoul (KR)

(73) Assignee: LG Electronics Inc., Seoul (KR)

(*) Notice: Subject to any disclaimer, the term of this patent is extended or adjusted under 35 U.S.C. 154(b) by 199 days.

(21) Appl. No.: 12/959,543

(22) Filed: Dec. 3, 2010

(65) Prior Publication Data

US 2011/0142413 A1 Jun. 16, 2011

Related U.S. Application Data

(60) Provisional application No. 61/266,933, filed on Dec. 4, 2009, provisional application No. 61/266,938, filed on Dec. 4, 2009.

(30) Foreign Application Priority Data

Mar. 3, 2010 (KR) .......................... 10-2010-0019139
Mar. 3, 2010 (KR) .......................... 10-2010-0019140

(51) Int. Cl.
*H04N 9/80* (2006.01)
(52) U.S. Cl.
USPC ............................................ 386/248; 348/51

(58) Field of Classification Search
USPC ............................... 386/241, 248, 344; 348/51
See application file for complete search history.

(56) References Cited

U.S. PATENT DOCUMENTS

| | | | | | |
|---|---|---|---|---|---|
| 5,676,138 | A | * | 10/1997 | Zawilinski | 600/301 |
| 7,120,880 | B1 | * | 10/2006 | Dryer et al. | 715/863 |
| 7,203,356 | B2 | * | 4/2007 | Gokturk et al. | 382/154 |
| 7,369,903 | B2 | * | 5/2008 | Diederiks et al. | 700/28 |
| 7,415,191 | B2 | * | 8/2008 | Sako et al. | 386/248 |
| 7,853,122 | B2 | * | 12/2010 | Miura et al. | 386/248 |
| 7,953,255 | B2 | * | 5/2011 | Amento et al. | 382/118 |

(Continued)

FOREIGN PATENT DOCUMENTS

| | | | |
|---|---|---|---|
| EP | 1 533 784 A2 | 5/2005 |
| EP | 1 533 785 A2 | 5/2005 |

(Continued)

OTHER PUBLICATIONS

Aucouturier et al., "Scaling Up Music Playlist Generation", IEEE, vol. 1, pp. 105-108, Aug. 26, 2002, XP010604317.

(Continued)

*Primary Examiner* — David Harvey
(74) *Attorney, Agent, or Firm* — Birch, Stewart, Kolasch & Birch, LLP

(57) ABSTRACT

An digital data reproducing apparatus and a method for controlling the same are discussed. The method includes obtaining, by the digital data reproducing apparatus, emotion information associated with at least one of a user and a content, modifying at least one of audio and video characteristics of a content for reproduction based on at least the emotion information, and reproducing the content based on the modified at least one of audio and video characteristics of the content.

23 Claims, 23 Drawing Sheets

(56) References Cited

U.S. PATENT DOCUMENTS

| | | | |
|---|---|---|---|
| 8,001,108 B2* | 8/2011 | Jung et al. | 707/713 |
| 8,159,504 B2* | 4/2012 | Chang et al. | 345/619 |
| 8,418,193 B2* | 4/2013 | Saito et al. | 725/12 |
| 2003/0063222 A1* | 4/2003 | Creed et al. | 348/687 |
| 2003/0081834 A1* | 5/2003 | Philomin et al. | 382/190 |
| 2003/0093784 A1* | 5/2003 | Dimitrova et al. | 725/10 |
| 2004/0013398 A1* | 1/2004 | Miura et al. | 386/46 |
| 2004/0105662 A1* | 6/2004 | Seo et al. | 386/95 |
| 2005/0089206 A1* | 4/2005 | Rice et al. | 382/128 |
| 2006/0094943 A1* | 5/2006 | Van Slyke | 600/323 |
| 2007/0011196 A1* | 1/2007 | Ball et al. | 707/104.1 |
| 2007/0208569 A1 | 9/2007 | Subramanian et al. | |
| 2007/0274679 A1* | 11/2007 | Yahata et al. | 386/69 |
| 2008/0101660 A1 | 5/2008 | Seo | |
| 2009/0304232 A1* | 12/2009 | Tsukizawa | 382/103 |
| 2010/0156897 A1* | 6/2010 | Blumenthal et al. | 345/419 |
| 2010/0309287 A1* | 12/2010 | Rodriguez | 348/43 |
| 2011/0109720 A1* | 5/2011 | Smolic et al. | 348/43 |
| 2011/0126160 A1* | 5/2011 | Han et al. | 715/848 |

FOREIGN PATENT DOCUMENTS

| | | | |
|---|---|---|---|
| EP | 1 973 114 A1 | | 9/2008 |
| WO | WO 2004/006570 | * | 1/2004 |
| WO | WO 2005/082471 A1 | | 9/2005 |

OTHER PUBLICATIONS

Oliver et al., "PAPA: Physiology and Purpose-Aware Automatic Playlist Generation", ISMR 2006., URL:http://ismir2006.ismir.net/PAPERS/ISMIR06162_Paper.pdf, Oct. 12, 2006, XP007910448.

Picard et al., "Affective Wearables", IEEE, pp. 90-97, Oct. 1997, XP010251547.

M. Vetter, "Dynamic Metadata Dictionary," Private SMPTE Technical Committee Document—Not for Publication, Proposed SMPTE Standard, Proposed SMPTE 335M, MPEG00/5927, Metadata Dictionary Structure, XP030035104, Mar. 14, 2000, pp. 1-12.

* cited by examiner (a)  (b)

(a)　　　　　(b)　　　　　(c)

(a)　　　　　(b)　　　　　(c)

(a)          (b)          (c)

(a)  (b)

(c)  (d)

DIGITAL DATA REPRODUCING APPARATUS AND CORRESPONDING METHOD FOR REPRODUCING CONTENT BASED ON USER CHARACTERISTICS

CROSS-REFERENCE TO RELATED APPLICATION

This application claims the benefit of U.S. Provisional Application Nos. 61/266,933 and 61/266,938 filed on Dec. 4, 2009 in the USPTO and the benefit of Korean Patent Application No. 10-2010-0019139, filed on Mar. 3, 2010 and Korean Patent Application No. 10-2010-0019140, filed on Mar. 3, 2010 in the Korean Intellectual Property Office. The entire contents of each of these applications are incorporated herein by reference.

BACKGROUND OF THE INVENTION

1. Field of the invention

The present invention relates to a digital data reproducing apparatus and a method for controlling the same, and more particularly, to a digital data reproducing apparatus and a method for controlling the same, which can reproduce content according to emotional information of a user.

2. Description of the Related Art

A digital data reproducing apparatus has a function of displaying images to a user. The digital data reproducing apparatus can display a broadcast program selected by the user on a display from among broadcast programs transmitted from broadcasting stations. The recent trend in broadcasting is a worldwide shift from analog broadcasting to digital broadcasting.

As it transmits digital audio and video signals, digital broadcasting offers many advantages over analog broadcasting, such as robustness against noise, less data loss, ease of error correction, and the ability to provide high-definition, clear images. Digital broadcasting also allows interactive viewer services, compared to analog broadcasting. In this digital broadcasting environment, Considerable efforts have focused upon enhancing the usability of digital data reproducing apparatuses.

SUMMARY OF THE INVENTION

Therefore, the present invention has been made in view of the above problems, and it is an object of the present invention to provide a digital data reproducing apparatus and a method for controlling the same, which can reproduce content according to emotional information of a user.

It is another object of the present invention to provide a digital data reproducing apparatus and a method for controlling the same, which can increase user convenience.

In accordance with an aspect of the present invention, the above and other objects can be accomplished by the provision of a method for controlling a digital data reproducing apparatus, including obtaining, by the digital data reproducing apparatus, emotion information associated with at least one of a user and a content, modifying at least one of audio and video characteristics of a content for reproduction based on at least the emotion information, and reproducing the content based on the modified at least one of audio and video characteristics of the content.

In accordance with another aspect of the present invention, there is provided a digital data reproducing apparatus including an image capturing unit configured to capture a video of a user to generate user image information, an audio recording unit configured to record audio data of the user to generate voice information of the user, a body signal sensing unit in a remote control unit, and configured to sense physical attributes of the user to generate physical information of the user, a controller configured to obtain emotion information associated with at least one of the user and a content, to modify at least one of audio and video characteristics of a content for reproduction based on at least the emotion information, and to reproduce the content based on the modified at least one of audio and video characteristics of the content, an interface unit configured to transmit the physical information of the user to the controller, and a network unit configured to communicate the emotion information with at least one of another user at another apparatus in a network.

In accordance with another aspect of the present invention, there is provided a method for controlling a digital data reproducing apparatus including obtaining, by the digital data reproducing apparatus, user image information of a user using at least two cameras, the at two cameras including a 3-D depth camera and an RGB camera, generating emotion information of the user based on the obtained user image information, and storing the generated emotion information of the user in the digital data reproducing apparatus.

In accordance with another aspect of the present invention, there is provided a method for controlling a digital data reproducing apparatus including receiving, by the digital data reproducing apparatus from a transmitting apparatus, (a) seamless reproduction information associated with a content displayed at the transmitting apparatus, and (b) emotion information associated with the content, modifying at least one of audio and video characteristics of the content based on the emotion information, and seamlessly reproducing, by the digital data reproducing apparatus, the content based on the seamless reproduction information and based on the modified at least one of audio and video characteristics of the content.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENTS

Embodiments of the present invention will be described below with reference to the attached drawings.

The terms "module" and "unit" are simply used herein to aid the understanding of the components and should not be considered as having specific meanings or roles. Accordingly, the terms "module" and "unit" may be used interchangeably.

Figure 1:
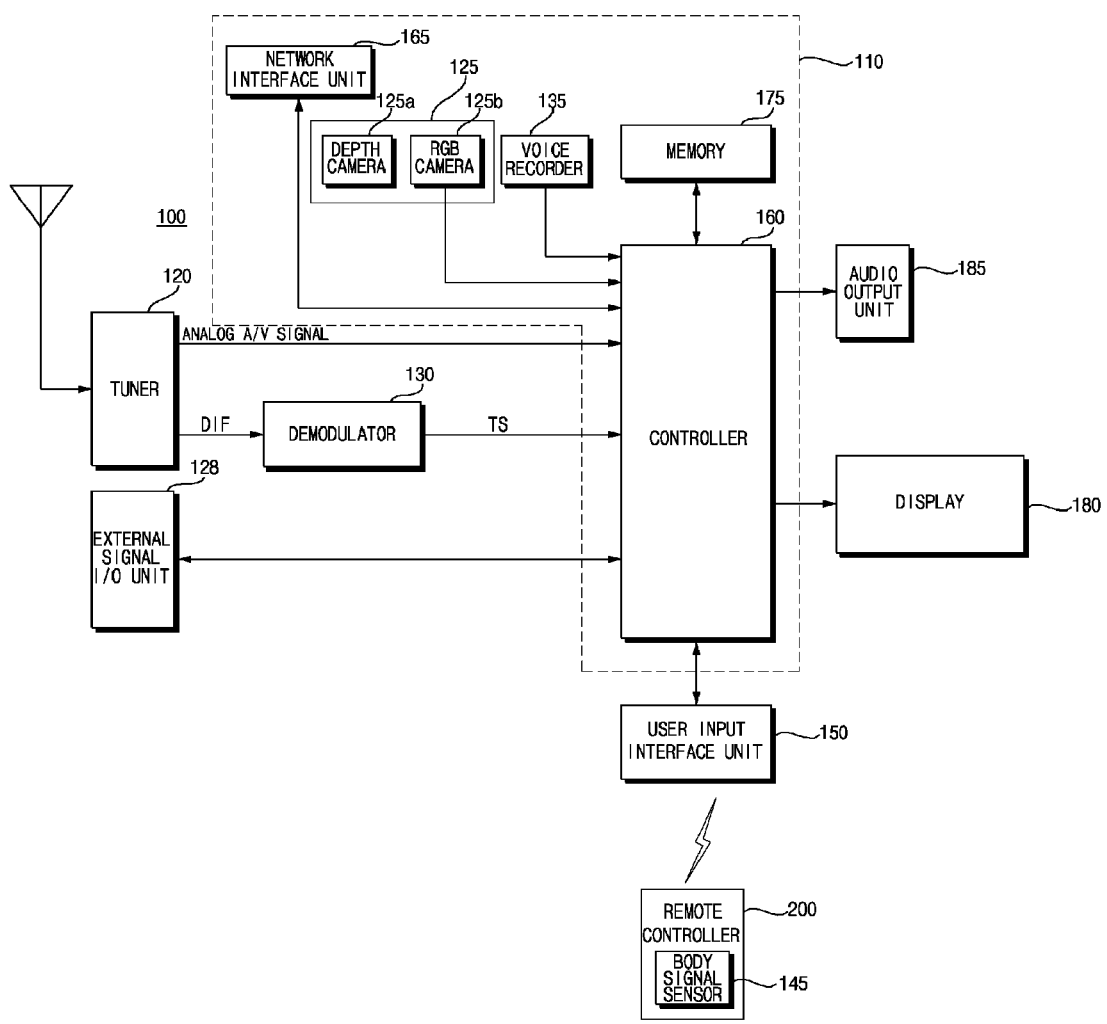
FIG. 1 is a block diagram of a digital data reproducing apparatus for reproducing content according to emotional information according to an embodiment of the present invention.
Figure 2:
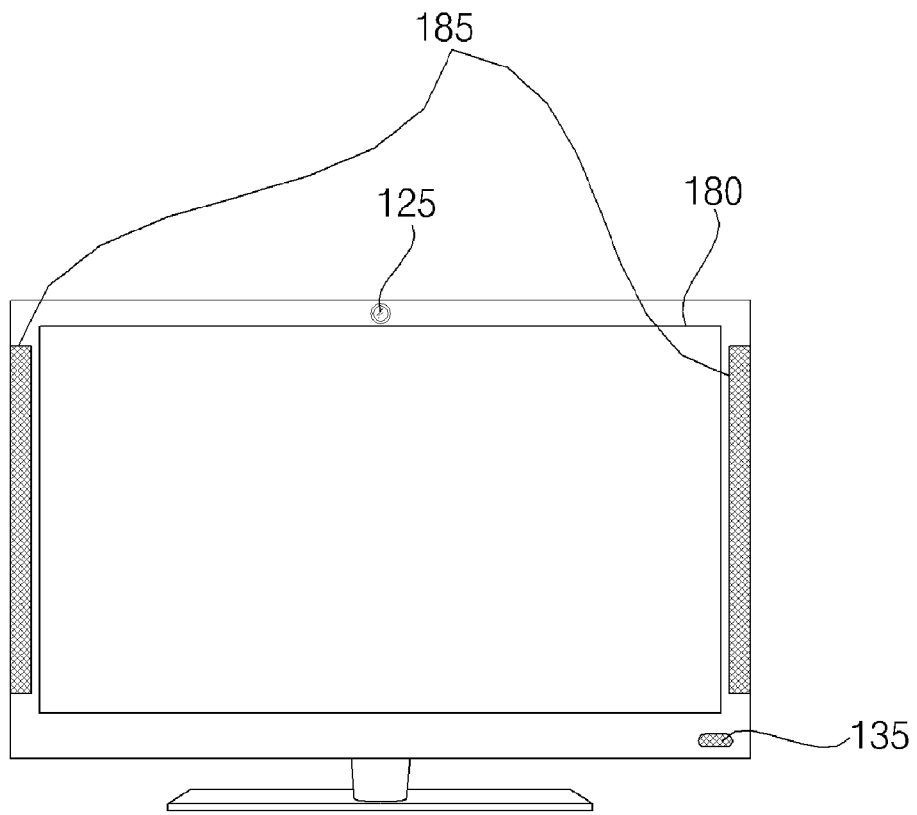
FIG. 2 is a simplified view of the exterior of the digital data reproducing apparatus illustrated in FIG. 1.
Figure 2:
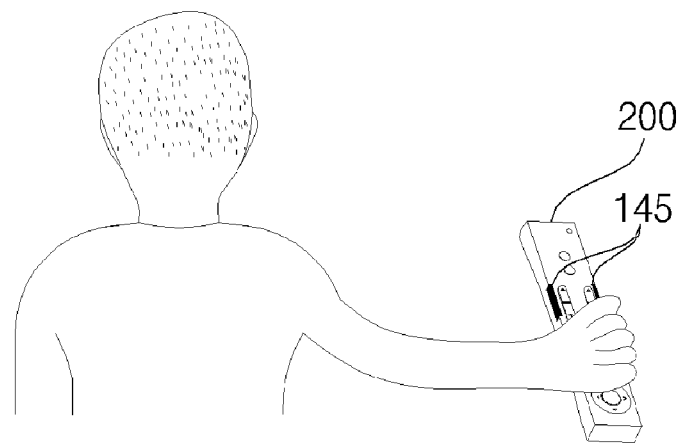
Figure 3:
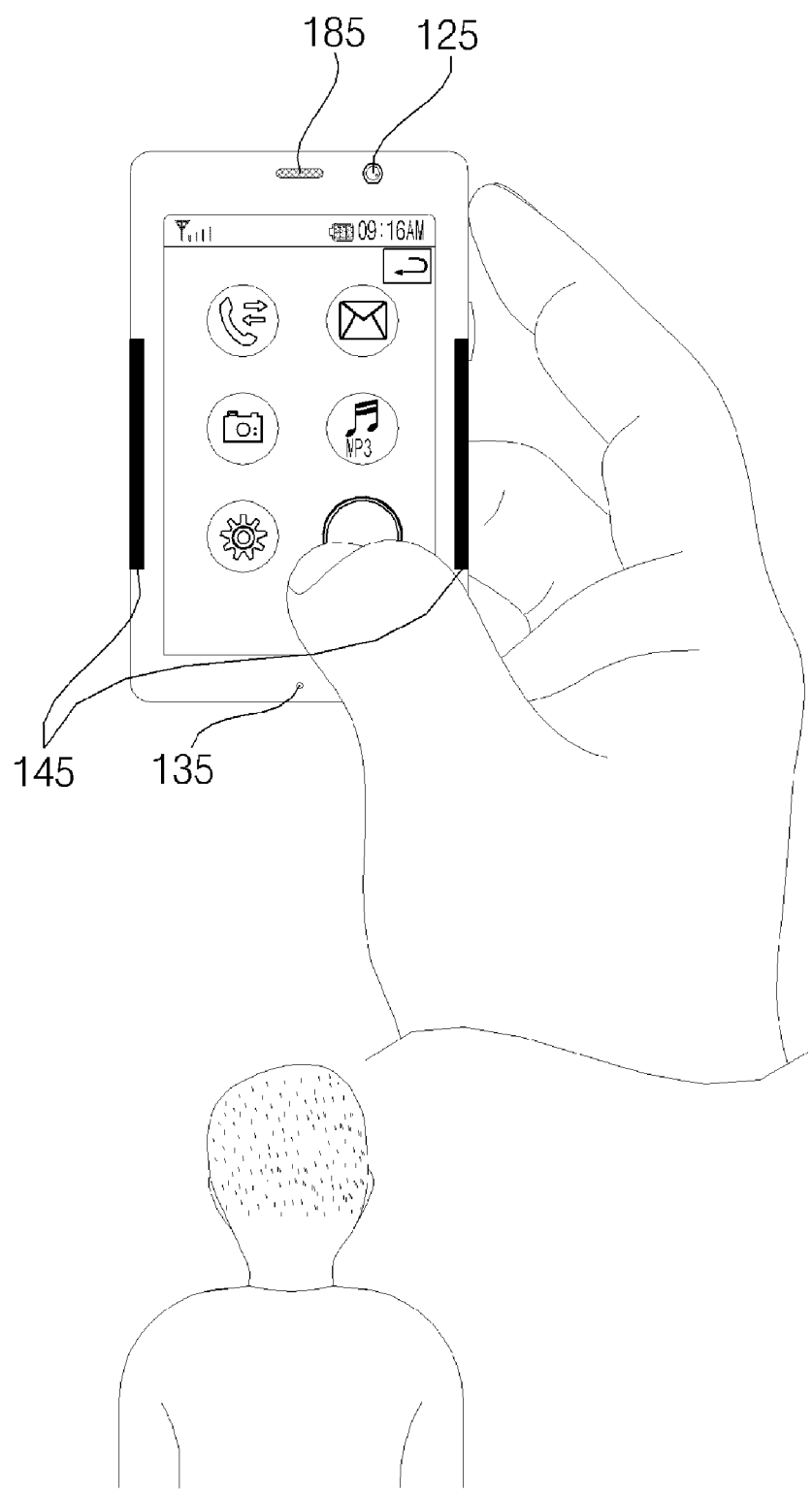
FIG. 3 is a simplified view of the exterior of a portable terminal.
Figure 4:
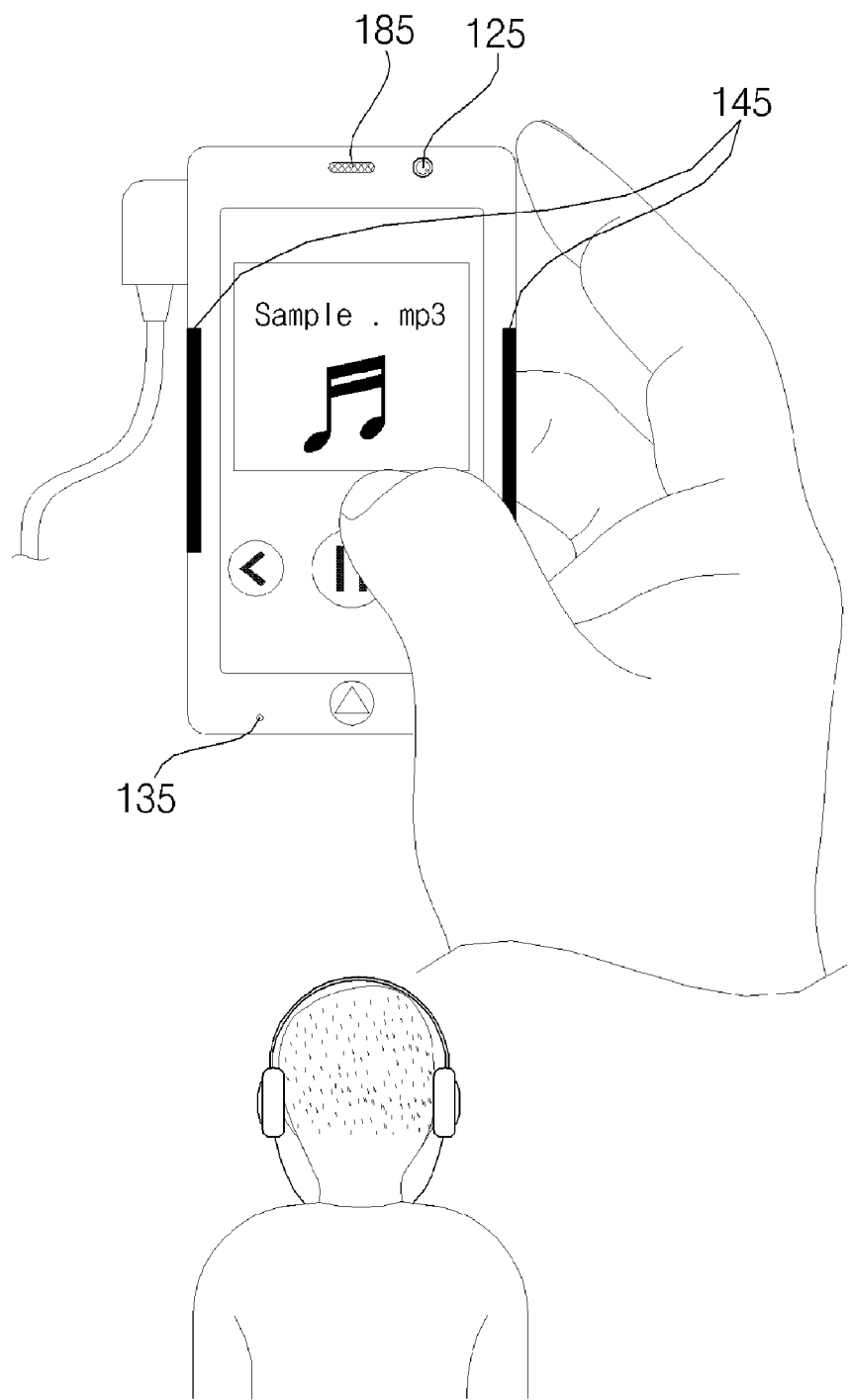
FIG. 4 is a simplified view of the exterior of a portable audio player.

FIG. 1 is a block diagram of a digital data reproducing apparatus for reproducing content according to emotional information according to an embodiment of the present invention, FIG. 2 is a simplified view of the exterior of the digital data reproducing apparatus illustrated in FIG. 1, FIG. 3 is a simplified view of the exterior of a portable terminal, FIG. 4 is a simplified view of the exterior of a portable audio player, and FIG. 5 illustrates an emotional map stored in a memory illustrated in FIG. 1.

Referring to FIG. 1, a digital data reproducing apparatus 100 may include a tuner 120, an external signal Input/Output (I/O) unit 128, a demodulator 130, an image capture unit 125, a voice recorder 135, a user input interface unit 150, a controller 160, a memory 175, a display 180, and an audio output unit 185. The digital data reproducing apparatus 100 may further include a network interface unit 165.

The tuner 120 selects a Radio Frequency (RF) broadcast signal of a channel selected by the user or RF broadcast signals of all of pre-stored channels from among RF broadcast signals received through an antenna. The tuner 120 also converts the selected RF broadcast signal into a digital Intermediate Frequency (IF) signal DIF or an analog baseband audio/video (A/V) signal.

First, the image capture unit 125 captures at least a part of a user's body. For instance, the image capture unit 125 may capture an image of the user's face, particularly specific parts of the face such as the eyes and eyebrows. To capture the user, the image capture unit 125 may be positioned at an upper end of the display 180. For example, the image capture unit 125 may be a camera, a camcorder, etc. The captured image is transmitted to the controller 160 generating emotional information. Further, the digital data reproducing apparatus 100 may include a plurality of image capture units 125. In addition, the image capture unit 125 may be installed at the outside of the digital data reproducing apparatus 100, or be embedded in the digital data reproducing apparatus 100.

Also, the image capture unit 125 may include two types of image capture units, for example, a depth camera 125a and a Red, Green, Blue (RGB) camera 125b. The depth camera 125a may be a Time Of Flight (TOF) camera or a Structured Light camera.

First, the TOF camera includes an infrared light source and an image sensor. The TOF camera emits an infrared ray from the infrared light source and measures the distance between an object by calculating a phase difference between the emitted infrared ray and an infrared ray reflected from the object. Further, the Structured Light camera projects a series of infrared patterns (multiple infrared points) onto an object from an infrared light source, captures patterns reflected from the object through an image sensor, and obtains the distance between the object and the Structured Light camera based on the warping of the reflected patterns.

On the other hand, the RGB camera 125b may include three image sensors (Complementary Metal Oxide Semiconductor (CMOS) image sensors), and obtain R, G and B color information. In comparison to the depth camera 125a, the RGB camera 125b obtains a relatively high-resolution image.

Despite the advantage of rapid recognition and processing of a fast motion or a motion made along a large trajectory, the depth camera 125a is disfavored when detecting a motion having a small trajectory and remotely detecting a motion because of its slow recognition rate. By contrast, the RGB camera 125b is capable of capturing a slow motion or a small-trajectory motion, or accurately capturing facial expressions. Accordingly, although the image capture unit 125 may capture a user's face using only one of the depth camera 125a and the RGB camera 125b, using two cameras provides a more accurate facial recognition. For example, the image capture unit 125 may extracts the coordinates of a captured user's face using the depth camera 125a. Then, based on the extracted coordinates, the RGB camera 125b may capture the more rapid and accurate facial expressions of the user. This face capturing scheme enables more efficient face recognition, for example, when the user is at a considerable distance from the image capture unit or when the user's facial expression changes rapidly. Irrespective of the distance to the user or the rapid change in the user's facial expression, the RGB camera 125b may capture accurate facial expressions based on facial coordinate information extracted from the depth camera 125a.

The above-described depth camera 125a and the RGB camera 125b are purely exemplary. Therefore, the present invention can be implemented using other types of capture devices for obtaining image information using the aforementioned methods.

Then, the captured image is provided to the controller 160. The image capture unit 125 may be, for example, a camera, a camcorder, or the like. The image capture unit 125 may be attached to an image display apparatus such as a TV shown in FIG. 2, a portable terminal shown in FIG. 3, a portable audio player such as an MP3 player shown in FIG. 4, or a remote controller 200 for controlling an electronic device such as an image display apparatus as shown in FIG. 2. Here, the captured image may be a still image or video.

Next, the external signal I/O unit 128 receives signals from an external device. For example, the external signal I/O unit 128 may be connected to an external device such as a Digital Versatile Disk (DVD) player, a Bluray player, a game player, a camcorder, a computer, etc. Here, the external signal I/O unit 128 may provide an external video signal, audio signal and data signal to the controller 160 of the digital data reproducing apparatus 100. In addition, the external signal I/O unit 128 may output processed video, audio and data signals received from the controller 160 to the external device.

Referring to FIG. 1, the demodulator 130 receives the digital IF signal DIF from the tuner 1820 and demodulates the digital IF signal DIF. In addition, the voice recorder 135 records the user's voice. For this purpose, the voice recorder 135 may be positioned at a lower end of the display 180. The recorded voice may be input to the controller 160 for generating emotional information.

Further, the body signal sensor 145 senses a user's body signal. To sense the user's body signal, the body signal sensor 145 may be carried with the user. For example, the body signal sensor 145 may be provided, for example, in the remote controller 200 of FIG. 2, the portable terminal shown in FIG. 3, or the portable audio recorder shown in FIG. 4, such as a MP3 player. Also, the body signal sensor 145 may be installed in an accessory such as a wrist watch, a pendant of a necklace, a pendant of a bracelet, a headset, and an earphone, in order to be in contact with the user's body. With the body signal sensor 145 in the remote controller or in the accessory worn on the user's body, a body signal may be sensed from the user, while the user may remotely control a multimedia player using the remote controller. Here, the sensed body signal is input to the controller 160 wirelessly or by a cable through the network interface unit 165. As illustrated in FIG. 4, brain waves of the user may be monitored through a headset of the portable audio player.

For example, the body signal sensor 145 may sense a galvanic skin response (GSR), a skin temperature (SKT), an electrocardiogram (ECG), an electromyograph (EMG), brain waves, a respiration, etc. The user's information about arousal, concentration, etc. may be monitored based on these vital signs. The GSR measures changes in the conductivity of the surface of a person's skin according to psychological state. Specifically, the GSR is a reflection of a sweat gland activity. The SKT is a change in a body surface temperature. The ECG is the pattern of the P, Q, R, S and T waves extracted as signals representing the minute electrical signals produced by the beating heart, amplified by a cardiograph. The EMG is an electrical recording of neuromuscular activities concerning muscular contraction and relaxation. The brain waves are divided into alpha waves, beta waves, slow waves, fast waves, etc. To sense brain waves, respiration speed, respiration depth, etc., the body signal sensor 145 may be a head mount (HT) type sensor.

The image captured by the image capture unit 125, the voice recorded by the voice recorder 135, and the body signal sensed by the body signal sensor 145 in FIGS. 2, 3 and 4 may be transmitted to an external network, for example, an external server or to other electronic devices within a short range by short-range communication, through the network interface unit 165, instead of being provided to the controller 160. A main electronic device serving as the server from among the electronic devices may process these signals.

Further, the body signal sensor 145 may be provided in the display 180. For example, when the display 180 is configured to be a touch screen or a touch pad, the body signal sensor 145 may be attached to the display 180 to sense a body signal when the user touches the display 180.

The user input interface unit 150 transmits an input signal received from the user to the controller 160 or a signal received from the controller 160 to the user. Especially, the user input interface unit 150 provides a body signal sensed by the body signal sensor 145 to the controller 160.

Next, the controller 160 provides an overall control to the digital image reproducing apparatus 100. In addition, the controller 160 may demultiplex an input stream into audio, video and/or data signals, for outputting an image and sound. Further, the controller 160 may include a demultiplexer, a video processor, an audio processor, an On Screen Display (OSD) generator, and an emotional information processor.

In addition, the controller 160 may determine the emotional state of the user based on at least one of the image captured by the image capture unit 125, the voice recorded by the voice recorder 135, or the body signal sensed by the body signal sensor 145. Here, the accuracy of the user's recognized emotional state may be increased using at least two of the received image, voice, and body signal. Further, the controller 160 may extract user's facial information from the captured image using a facial information extraction algorithm. Many facial information extraction algorithms are available, which will not be described herein because the focus is not upon them.

First, upon receipt of the captured image from the image capture unit 125, the controller 160 may determine the emotional state of the user by comparing the captured image with reference images. For example, the reference images may be a number of images of facial expressions representing various emotional states. In addition, the reference images may be retained in a network, not in a local memory.

Further, the controller 160 may extract a facial image from the captured image and compare user's facial image with the reference images. Alternatively or additionally, the controller 160 may extract a plurality of feature points from the extracted facial image and compare the distances between the feature points of the extracted image with the distances between features points in the reference images. Here, the plurality of feature points may be located on at least two facial parts selected from the eyes, the eyebrows, the nose, the mouth, the ears, and the philtrum.

A Facial Action Coding System (FACS) algorithm and a fuzzy rule based algorithm may be utilized to determine the emotional state of the user. The FACS algorithm divides the movement of facial muscles into 44 Action Units (AUs) each corresponding to a visual change in a facial expression and identifies an emotional state using combinations of the AUs. On the other hand, the fuzzy rule based algorithm determines an emotional state using facial feature points and parameters by fuzzy inference. In this manner, the controller 160 may recognize various emotional states using a reference image most closely approximating the captured image. Further, the emotional states may be categorized into joy, sadness, anger, surprise, fear, disgust, composure, anxiety, friendly, hostile, excitement, etc.

Meanwhile, the controller 160 may process the captured image and determine the emotional state of the user using the processed image only when a variation is detected from the image captured by the image capture unit 125. For instance, if the variation of at least one facial part from among the eyes, eyebrows, nose, mouth, ears, or philtrum of the user's face in size, position, shape, color or motion is equal to or larger than a predetermined value, the controller 160 may determine that the emotional state of the user is changed based on the changed size, position, shape and/or color of the at least one facial part. Here, a valid captured image may be a frontal face of the user. In this case, the controller 160 may generate emotional information, referring to images captured by a plurality of image capture units, a recorded voice or a sensed body signal.

Secondly, upon receipt of the recorded voice from the voice recorder 135, the controller 160 may determine the emotional state by comparing the recorded voice with reference voices. Alternatively or additionally, the controller 160 may determine the emotional state by processing the recorded voice only when a variation of the recorded voice exceeds a predetermined value. Especially, the controller 160 may determine the emotional state based on the pitch, intensity, pace, etc. of the voice. For example, the emotional state can be identified based on a Log Frequency Power Coefficient (LFPC) feature vector of intensities of voice that has passed through the filters of a filter bank.

Further, the controller 160 may determine the emotional state of the user, comprehensively taking into an account the image captured by the image capture unit 125, the voice recorded by the voice recorder 135, and the body signal sensed by the body signal sensor 145. For example, the user's emotional information may be generated separately using the captured image and the recorded voice. Next, common emotional information may be extracted by comparing the two pieces of the user's emotional information, thereby increasing the accuracy of the emotional information. Alternatively, the emotional information may be generated separately using the captured image and the sensed body signal and then combined, or be generated separately using the recorded voice and the sensed body signal and then combined.

Here, the captured image, the recorded voice and the body signal may be assigned different weights thereby generating the user's emotional information in proportion to the significance of the signals. For instance, recorded voices of a plurality of users may be inaccurate. Thus, the recorded voices may be weighted less heavily than captured images of the plurality of users. On the other hand, if the user is moving, the weight of the user's recorded voice may be higher than the other factors including a captured image and/or a sensed body signal. Therefore, the user's emotional state may be identified more accurately, taking into an account the situation in which the user is.

Further, the emotional states of the plurality of users may be determined separately and then combined to yield a representative emotional state. Specifically, the emotional state of each user may be determined mainly based on a captured image or sensed body signal of each rather than recorded voice of the each user. Here, a determined mean value of the emotional states of each user may be the representative emotional state of the plurality of the users. Further, if a specific content is being reproduced for the plurality of users, the emotional states of the users may be recognized separately and a representative emotional state may be determined for the reproduced content based on the emotional states in the above manner. In addition, when the emotional information of each user is generated, that is, the individual's emotional state is determined, image information or physical information of the individual may be more heavily weighted than voice information of the individual.

Emotional states of the user may be monitored over time and the representative emotional state of the user (i.e. the representative emotional curve of the user) may be calculated by averaging the emotional states. Further, a different weight may be assigned to each user according to the category of the content being reproduced and representative emotional information may be generated for the plurality of users according to the weight assigned to each user. For instance, when displaying an image for kids, a higher weight may be applied to emotional information of a child, who is what the image than emotional information of an adult watching the image together with the child, to thereby create representative emotional information for the child and the adult.

Meanwhile, the controller 160 may generate attention information of the user based on at least one of the user's motions, a viewing duration of reproduced content, a volume down/up, or the length of time the user fixes his or her gaze on the content. Here, the presence or absence of the user's motion or the magnitude of the motion, and the length of time the user fixes his or her gaze on the content may be obtained by the image capture unit 125. The attention information may be used to determine the intensity of the user's emotion or the reliability of the user's emotional information. That is, a specific scene or a content which the user has concentrated on may increase the reliability of the intensity of the representative emotion about the scene or the content. Here, when a plurality of users is present, representative emotional information may be created based on attention information and emotional information of the individual users.

Further, the controller 160 may generate emotional intensity information based on at least one of image information, voice information or physical information of a user. For example, if the user has made large gestures or the volume of the user's voice that equals or exceeds a predetermined value, the user's emotional intensity information representing the intensity of emotion that the user feels may be generated in addition to emotional information representing the type of the emotion.

The controller 160 may control a generation of an icon or avatar representing the identified emotional state of the user and then control displaying of the icon or avatar together with a specific scene, frame (frames), and content on the display 180.

When content is reproduced, the controller 160 may change the reproduction state of the content based on current emotional information of a user, generated in the afore-mentioned manner. That is, at least one of the visual or audio of the content may be changed according to the emotional information of the user. If the content is reproduced for pre-stored emotional information, the reproduction state of the content may be changed according to the pre-stored emotional information.

For instance, if the current emotional state of the user watching the content being reproduced is determined as sad or if emotional information previously stored for the content is sadness, the content may take on a blue visual tone or the bass sound of the content, which identifies with sadness, may be emphasized.

On the other hand, if the current emotional state of a user watching the content being reproduced is determined as joy or any other positive emotion or if emotional information previously stored for the content is joy or any other positive emotion, the content may take on a yellow or red visual tone, or the volume or frequency of the content may be increased, which identifies with joyfulness. In addition, a three-dimensional (3D) effect may be reinforced based on the positive emotion. Therefore, the user can become more absorbed in viewing the content.

When the pre-stored emotional information is available for reproducing the content, a decision is made as to whether to change the reproduction state of the content based on the current emotional state of the user or the pre-stored emotional information for the content. According to system settings, the current emotional state of the user or the pre-stored emotional information for the content may be selected. Alternatively, the user may be prompted to select between the current emotional state of the user or the pre-stored emotional information for the content, for content reproduction.

Figure 12:
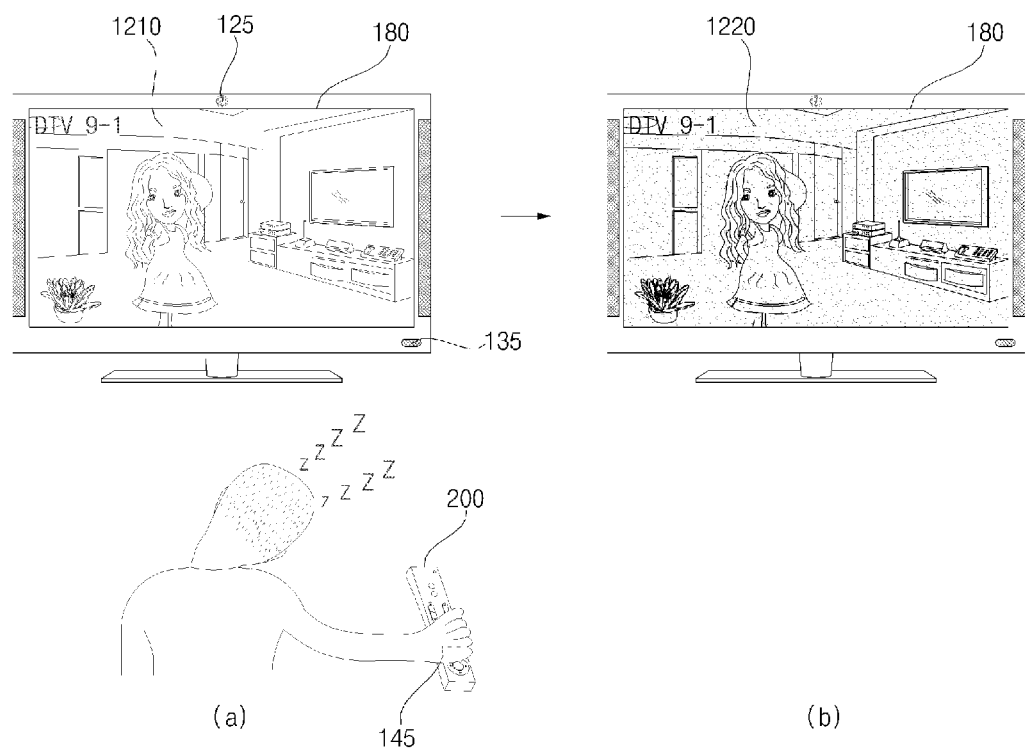

Further, the reproduction conditions of the content may be changed based on attention information that is elicited from a captured image, recorded voice, and/or a sensed body signal of the user, in addition to the emotional information. For example, as shown in FIG. 12, when the user dozes off, an image of the reproduced content may be displayed dark, may be scaled down, or the sound volume of the reproduced content may be turned down. In addition, an object indicating to the user whether to reproduce the content based on emotional information may be displayed in the form of a pop-up menu, a pull-down menu, etc. (refer to FIG. 10).

Figure 11:
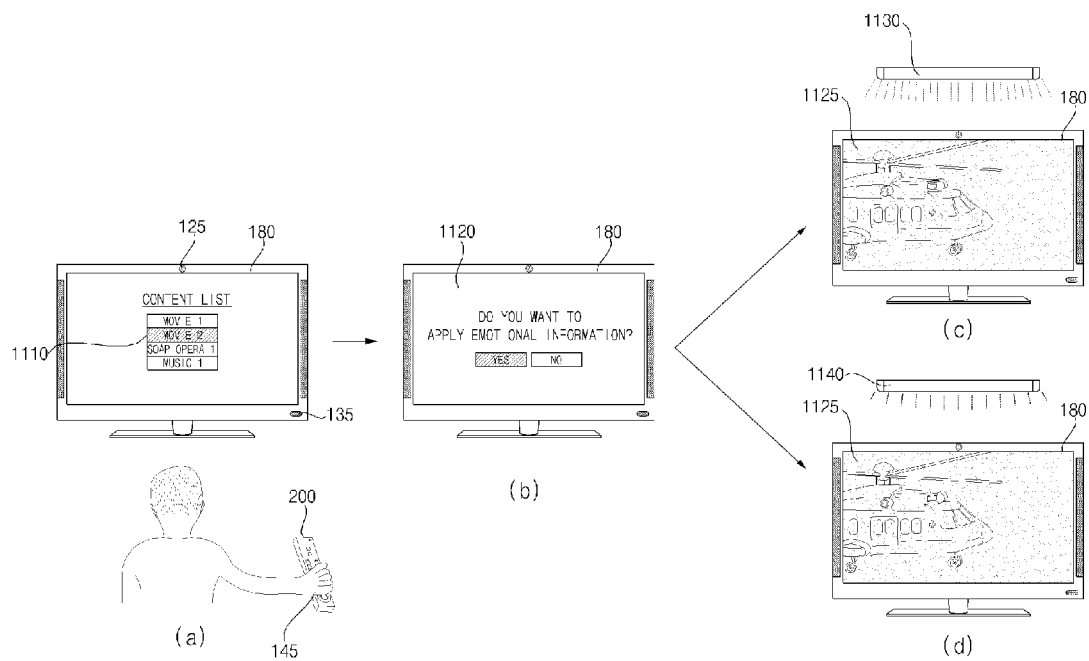

Also, referring to FIG. 11, the controller 160 may control an ambient lighting of the digital data reproducing apparatus 100 reproducing the content according to emotional information. Additionally, referring to FIG. 13, the controller 160 may change at least one of the image and the sound of the content being reproduced according to emotional information and emotional intensity information. As shown in FIG. 14, the controller 160 may also change at least one of the image and the sound of the content being reproduced according to the ambient lighting of the digital data reproducing apparatus 100 (refer to FIG. 14). Further, in FIG. 15, if a 3D image is received, the controller 160 may change the depth of the 3D image based on emotional information.

The controller 160 may also include a formatter for separating an input 3D image into a left-eye image and a right-eye image and arranging the left-eye and right-eye images in a predetermined format. Then, the controller 160 may control the depth of the 3D image by adjusting the disparity between the left-eye and the right-eye images according to the emotional information. For instance, if the emotional state is "joy", the 3D image may look more protruding by enlarging the disparity between the left-eye and right-eye images. On the other hand, if the emotional state is "sadness", the 3D image may look receding by shortening the disparity between the left-eye and right-eye images.

By and large, five 3D formats are available, Side by Side, Frame Sequential, Top/Down, Interlaced, and Checker Box. The left-eye image and the right-eye image are arranged side by side in the Side by Side format, in time division in the Frame Sequential format, up and down in the Top/Down format, alternately in odd-numbered and even-numbered lines in the Interlaced format, and in boxes according to a checkered pattern in the Checker Box format.

Figure 16:
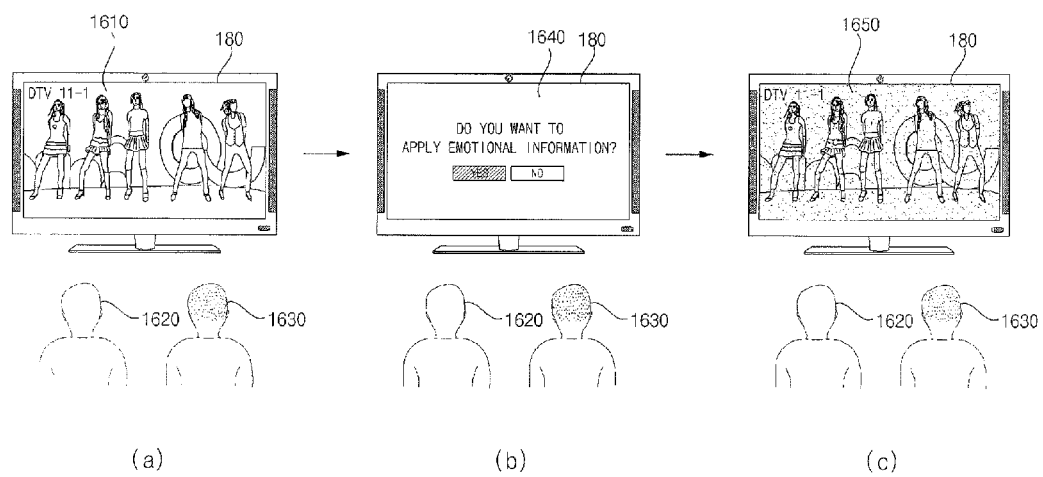

Referring to FIG. 16, when a plurality of users are present, the controller 160 may change at least one of the image and sound of reproduced content according to representative emotional information of the users. Especially, referring to FIG. 17, the representative emotional information may be created by assigning different weights to the users according to the category of the reproduced content and at least one of the image and sound of the reproduced content may be changed according to the representative emotional information. For instance, when an image for kids is displayed, a higher weight is applied to emotional information of a child than emotional information of an adult watching the image together with the child, to thereby create representative emotional information for the child and the adult. At least one of the audio and the video characteristics of the reproduced content may then be changed according to the representative emotional information.

Figure 18:
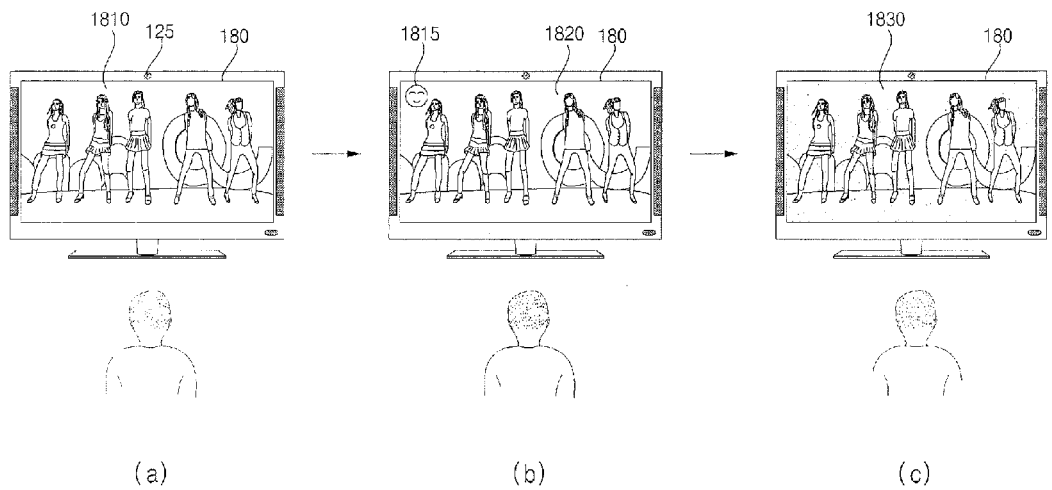
Figure 19:
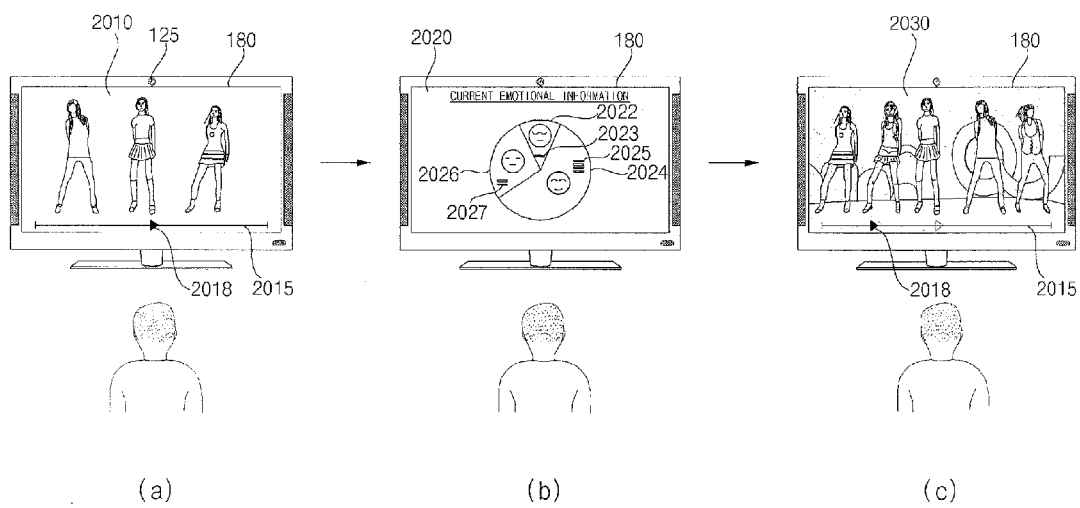

Further, as shown in FIG. 18, the controller 160 may control display of an object indicating emotional information of a user on the display 180. In addition, as shown in FIG. 19, if a user feels at least two emotions, the controller 160 may control display of an object indicating information representing the at least two emotions on the display 180.

Figure 20:
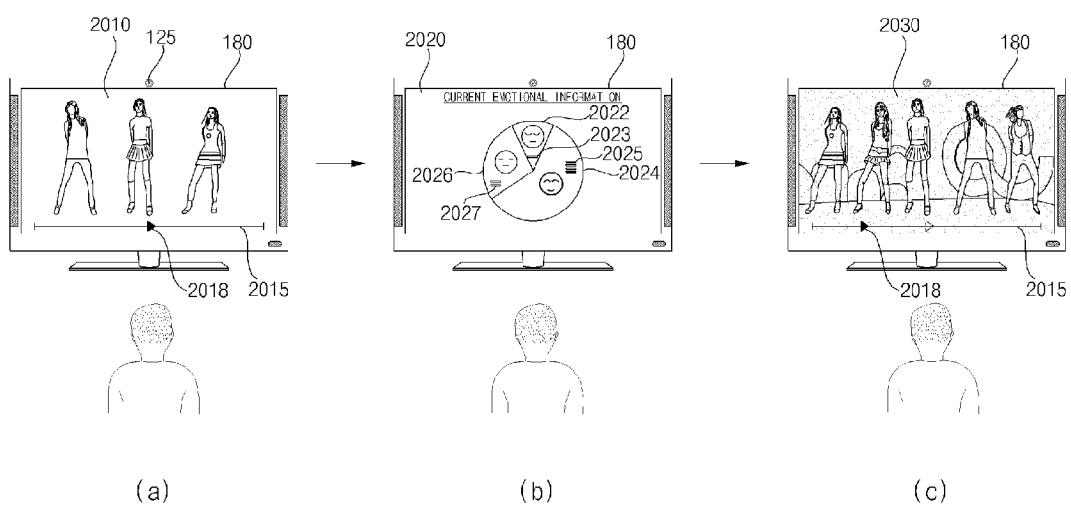

When the content is reproduced, as shown in FIG. 20, the controller 160 may control displaying of an emotional information menu indicating emotional information stored in the memory in combination with the content on the display 180. Here, the emotional information menu may include emotional information representing the type of emotion, emotional intensity information or attention information.

Upon selection of specific emotional information or specific emotional intensity information, the controller 160 may control reproducing a part of the content corresponding to the selected emotional information or emotional intensity information. Therefore, the part of the content corresponding to desired emotional information can readily be reproduced. Even when the content reproduction condition has been changed, the controller 160 may continue to obtain emotional information of the user and store the emotional information in the memory 175. The emotional information may be stored in conjunction with the content or may be stored independently.

The controller 160 may also control the tuner 120 to tune to a selected channel or a pre-stored channel and thus to receive an RF signal on the channel. Further, the controller 160 may process the video signal, audio signal, and data signal obtained by multiplexing the input stream. The controller 160 may also control the brightness, tint, color, etc. of the processed video signal. In addition, controller 160 may perform an OSD processing. For example, the controller 160 may generate a signal for displaying graphics or text on the display 180. The generated signal may be input to the display 180 together with the processed video signal and data signal. The controller 160 may also determine a rating by comparing the facial information and the voice information stored in the memory 175 with the extracted facial and voice information. In addition, the controller 160 may set a rating according to a user input and may update the rating.

Referring to FIG. 1, the network interface unit 165 may transmit or receive data wirelessly or by a cable, for example, to and from local electronic devices within a short range, and may connect to the Interface. In accordance with an embodiment of the present invention, the network interface unit 165 may transmit or receive user's emotional information to or from other electronic devices or an external network server, under the control of the controller 160.

The memory 175 may store programs necessary for the controller 160 to process and control signals, and may also store processed video, audio and data signals. The memory 175 may also retain an emotional map illustrated in FIG. 5A. The emotional map 500 may include an emotion type table 510, a user table 520, a location table 530, a content table 540, a product table 550, and a cast table 560.

Figure 5A:
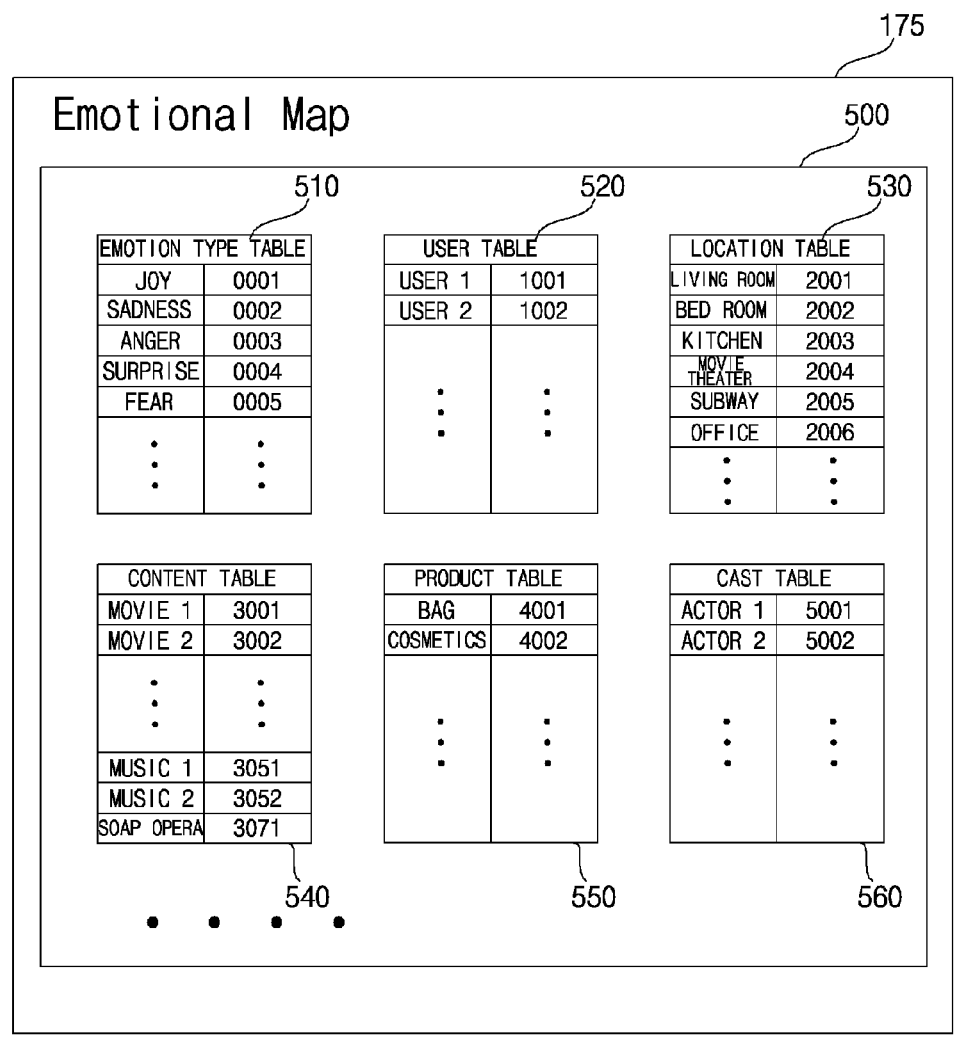
FIG. 5A illustrates an emotional map stored in a memory illustrated in FIG. 1.

Referring to FIG. 5A, the emotion type table 510 tabulates quantitative numerical data of various emotional states of the user. For instance, each value representing an emotional state may be created by comprehensively quantifying facial information, voice information and a body signal indicative of the specific emotional state of the user. Here, the controller 160 may retrieve the pre-stored emotion type table 510, quantify emotional information of a user, and store the emotional information in the memory 175. Meanwhile, the memory 175 may store the emotion information generated based on the emotion type table 510 in combination with at least one of user information of the user table 520, location information of the location table 530, content information of the content table 540, product information of the product table 550 or cast information of the cast table 560.

Figure 5B:
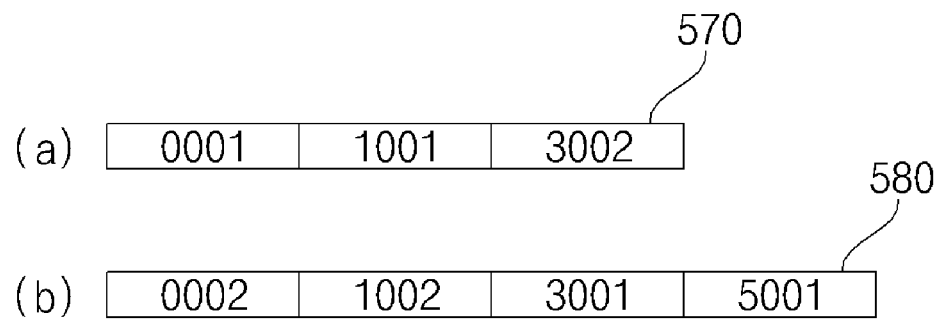
FIG. 5B illustrates a various emotional information file format using the emotional map illustrated in FIG. 5A.

FIG. 5B illustrates a various emotional information file formats using the emotional map illustrated in FIG. 5A. For example, as shown in FIG. 5B(a), emotional information file format 570 stored in memory 175 may include emotion information '0001' using the emotion type table 510, user information '1001' using the user table 520, and the content information '3002' using the content table 540. Also, as shown in FIG. 5B(b), emotional information file format 580 stored in memory 175 may include emotion information '0002' using the emotion type table 510, user information '1002' using the user table 520, content information '3001' using the content table 540, and cast information '5001' using the cast table 560. In addition to the above mentioned examples, variations of emotional information file formats may be generated within the scope of the present invention.

In addition, the emotional information may be time-stamped to indicate when the emotional information was generated for the reproduced content. Here, the representative emotional information may be stored based on the content. The emotional information may be stored in combination with at least one of the age, gender, location, or hobby of the user. In the case of a plurality of users, the emotional information may be stored in combination with information about the average age of the users. This combined emotional information may be included in the content or may be stored separately from the content.

To ensure compatibility with other electronic devices, each table may be standardized. If tables are created according to different standards, the tables may be converted between the standards. For example, if a table of a different standard is received from the network, the table may be converted suitably for the memory 175.

The memory 175 may transmit and/or the stored emotional information to another electronic device or a network server through the network interface unit 165, and store the received emotional information. For instance, content providers may build a database of emotional information by the content category, user, taste, age, region, gender, etc. in their servers.

Further, emotional information of users may be collected based on a particular content by sharing emotional information with other electronic devices or external servers. This content may be categorized by eliciting user's emotional response. Further, the representative emotional state for the content may be frequently updated based upon emotional responses of a plurality of users. Information about the representative emotional state for the content is transmitted to each electronic device and is provided to users viewing the content for use in comparison.

The content providers may receive the afore-described emotional information through the network interface unit 165. Since the emotional information is generated based on at least one of the captured image, the recorded voice, or the sensed body signal, the emotional information becomes more reliable.

Next, the memory 175 may also store at least one of attention information or emotional intensity information as well as emotional information of the user. The memory 175 may also temporarily store video, audio and/or data signal received from the external signal I/O unit 128. Additionally, the memory 175 may store broadcast channels using a channel add function. Further, while the memory 175 may be configured separately from the controller 160, the memory 175 may also be incorporated into the controller 160. The digital image reproducing apparatus 100 may reproduce the content stored in the memory 175 (e.g. video files, still image files, music files, text files, and application files) to the user.

Referring to FIG. 1, the display 180 may convert a processed video signal, a processed data signal, and an OSD signal received from the controller 160 or a video signal and a data signal received from the external device I/O unit 128 into RGB signals, thereby generating drive signals. The display 180 may be various types of displays, such as a 3D display. The display 180 may also be a touch screen that can be used not only as an output device but also as an input device.

The audio output unit 185 may receive the processed audio signal (e.g. a stereo signal, a 3.1 channel signal or a 5.1 channel signal) from the controller 160 and output the received audio signal as sound. The audio output unit 185 may employ various speaker configurations.

The remote controller 200 transmits a user input to the user input interface unit 150. For transmission of the user input, the remote controller 200 may use various communication techniques such as Bluetooth, RF communication, InfraRed (IR) communication, Ultra WideBand (UWB) and ZigBee. Further, the remote controller 200 may include the body signal sensor 145. The remote controller 200 may also receive video, audio and data signals from the user input interface unit 150 and output the received signals.

Further, the digital data reproducing apparatus 100 may be any of a TV receiver, a portable phone, a PC, a digital broadcasting terminal, a Personal Digital Assistant (PDA), a Portable Multimedia Player (PMP), etc. At least one of digital image reproducing apparatuses illustrated in FIGS. 2, 3 and 4 may not include the tuner and the demodulator.

Next, the controller 160 may include an emotion decision module to determine the emotional state of a single user or the emotional states of a plurality of users based on image information, voice information and physical information received from the image capture unit 125, the voice recorder 135, and the body signal sensor 145. The emotion decision module may contain algorithms for determining the emotional state of a user based on each of a captured image, recorded voice, and a sensed body signal.

The emotion decision module may include an algorithm for collecting the emotional information of the user determined by each algorithm and finally determining the emotional state of the user based on the collected emotional information according to a predetermined criteria. The predetermined criteria may be user conditions such as a single user, a plurality of users, a user's motion, or external environmental conditions such as noise, luminance, temperature, humidity, etc.

That is, the controller 160 may be a unit in which programs containing a variety of algorithms are stored and executed to extract, convert, store, and transmit information necessary to determine the emotional state of a user in addition to controlling various other components.

Further, the digital data reproducing apparatus according to an embodiment of the present invention may not include display 180. For example, a portable audio player such as an MP3 player (see FIG. 4) may not include display 180.

The block diagram of the digital data reproducing apparatus 100 illustrated in FIG. 1 is purely exemplary. Depending upon the specifications of the digital data reproducing apparatus 100 in actual implementation, the components of the digital data reproducing apparatus 100 may be combined or omitted or new components may be added. That is, two or more components are incorporated into one component or one component may be configured as separate components, as needed. In addition, the function of each block is described for the purpose of describing the embodiment of the present invention and thus specific operations or devices should not be construed as limiting the scope and spirit of the present invention.

Figure 6:
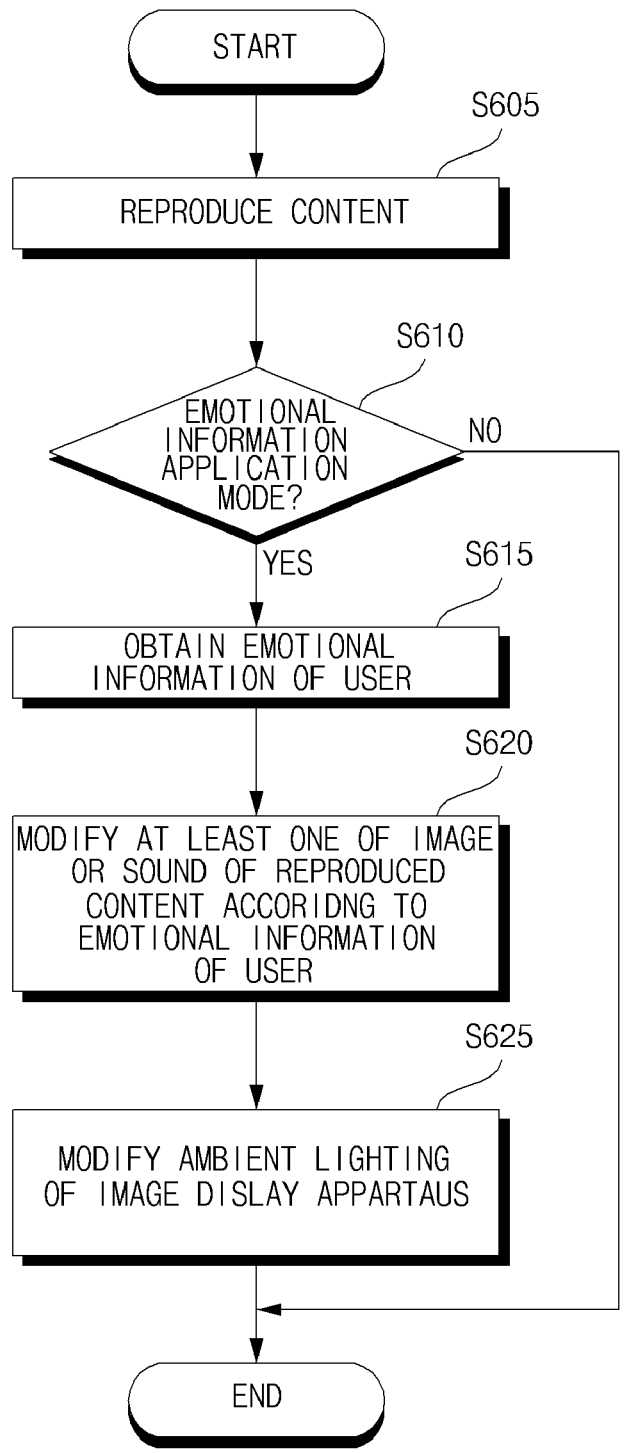
FIG. 6 is a flowchart illustrating a method for controlling the digital data reproducing apparatus according to an embodiment of the present invention.
Figure 7:
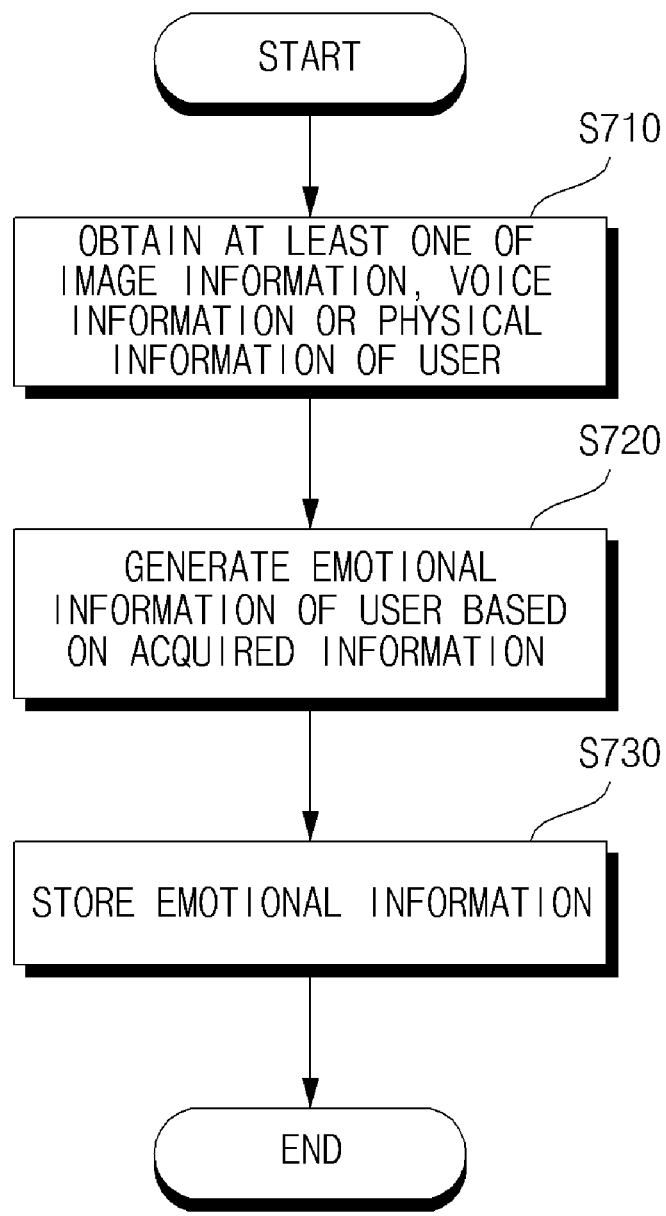
FIG. 7 is a detailed flowchart illustrating a step for obtaining emotional information in the method for controlling the digital data reproducing apparatus illustrated in FIG. 6.

FIG. 6 is a flowchart illustrating a method for controlling the digital data reproducing apparatus according to an embodiment of the present invention, FIG. 7 is a detailed flowchart illustrating a step for obtaining emotional information in the method for controlling the digital data reproducing apparatus illustrated in FIG. 6, and FIGS. 8 to 23 are views referred to for describing the digital data reproducing apparatus for reproducing content according to emotional information according to the embodiment of the present invention.

Referring to FIG. 6, first the digital data reproducing apparatus 100 reproduces the content selected by a user (S605). The reproduced content may be any of the image content such as a movie, a soap opera, a sport game, a documentary, an image, etc., the audio content such as a music, and the text content such as documents. The reproduced content may also be an external image received from an external device or a broadcast image obtained from a received broadcast signal.

Subsequently, the digital data reproducing apparatus 100 determines whether an emotional information application mode has been set (S610). If the digital data reproducing apparatus 100 is in the emotional information application mode, the digital data reproducing apparatus 100 obtains emotional information associated with at least one of the user and the content (S615). As illustrated in FIGS. 8(b), 9(b), 10(b) and 11(b), the emotional information application mode may be entered upon a user selection, with an object asking whether to reproduce content according to the emotional information of the user displayed on the display. Alternatively or additionally, the digital data reproducing apparatus 100 may automatically monitor the emotional state of the user. Further, if the digital data reproducing apparatus 100 determines that the emotional state of the user is a specific emotion such as joy, sadness, anger, etc., the digital data reproducing apparatus 100 may automatically enter the emotional information application mode when reproducing content.

In accordance with an embodiment of the present invention, the emotional information of the user may be obtained by monitoring the current emotional state of the user or may be received from a local electronic device or a network server. Alternatively, the user may pre-store emotional information and the pre-stored emotional information may be retrieved from the memory 175.

More specifically, upon the user request for reproducing the specific content in the emotional information application mode without any previously generated emotional information for the content, the digital data reproducing apparatus 100 collects the emotional information of the user. At the same time, the digital data reproducing apparatus 100 reproduces the content and modifies the reproduction condition of the content based on the collected emotional information. On the other hand, if the previously generated emotional information for the selected content exists, the digital data reproducing apparatus 100 may reproduce the content according to the previously generated emotional information.

Even though the specific content has previously set emotional information, the digital data reproducing apparatus 100 may also reproduce the specific content based on the current emotional state of the user. Here, the current emotional state of the user may be identified during the content reproduction, without using the already existing emotional information, according to the user selection or depending on the system settings. Further, the user may manually select emotional information to be applied when reproducing the selected content by using, for example, a menu screen. That is, the digital data reproducing apparatus 100 may reproduce the content based on the user-selected emotional information.

The obtaining step (S615) may include receiving, by the digital data reproducing apparatus 100, the content and the emotion information associated with the content from a server or a broadcast station or a storage unit of the digital data reproducing apparatus 100. Further, the obtaining step (S615) may include at least two of obtaining representative emotion information associated with at least one of the user and the content, obtaining emotion information for each scene or frame of the content, or obtaining emotion information for each time period associated with the content. Also, the obtaining step (S615) may further include receiving the user's selection of the emotion information among the at least two of the representative emotion information, the emotion information for each scene or frame, and the emotion information for each time period. In addition, the obtaining step (S615) may include pre-stored emotion information and real-time emotion information. Then, the digital data reproducing apparatus 100 may receive the user's selection of the emotion information among the pre-stored emotion information and the real-time emotion information. Meanwhile, the obtaining step (S615) may also include obtaining at least one of attentiveness information of the user and emotion intensity information associated with at least one of the user and the content.

Next, the digital data reproducing apparatus 100 modifies at least one of the audio and video characteristics of the content for reproduction based on at least the emotion information of the user (S620). Here, alternatively, the digital data reproducing apparatus 100 may modify the at least one of the audio and video characteristics of the content based on the user-selected emotion information. Then, the digital data reproducing apparatus 100 reproduces the content based on the modified at least one of audio and video characteristics of the content. At least one of the brightness, tint, color or size of the image of the reproduced content may be modified or at least one of the bass, treble or volume of the sound of the reproduced content may be modified. Meanwhile, the modifying step (S620) may be performed automatically or based on an input from the user. Also, the modifying step (S620) may modify the at least one of audio and video characteristics of the content based on the user-selected emotion information among the at least two of the representative emotion information, the emotion information for each scene or frame, and the emotion information for each time period. Further, the modifying step (S620) may modify the at least one of audio and video characteristics of the content based on the emotion information and based on at least one of the attentiveness information and the emotion intensity information.

Then, the digital data reproducing apparatus 100 modifies its ambient lighting for the digital data reproducing apparatus 100 based on the emotion information (S625), which will be detailed later with reference to FIG. 10.

FIG. 7 illustrates an operation for generating emotional information of a user. Referring to FIG. 7, first, the digital data reproducing apparatus 100 obtains at least one of user image information from at least one camera, voice information of a user, and physical information of the user from at least one body sensor (S710). Here, the obtaining step (S710) may be performed in real time while the user is viewing the content at the digital data reproducing apparatus. Thereafter, the digital data reproducing apparatus 100 generates the emotion information of the user based on the obtained information (S720). Then, the generated emotional information is stored in the memory 175 (S730).

As described before, the image information, voice information and physical information of the user may be obtained respectively from the image capture unit 125, the voice recorder 135, and the body signal sensor 145. The controller 160 generates the emotional information of the user by combining the image information, voice information and physical information. Specifically, the controller 160 may assign different weights to the image information, voice information and physical information, for generation of the emotional information. When a plurality of users is present, the controller 160 may generate the emotional information of the individual users and determine representative emotional information of the users based on the individuals' emotional information. In addition to the emotional information, emotional intensity information or attention information may be generated.

Further, the user image information of a user may be obtained using at least two cameras, for example a 3-D depth camera 125*a* and an RGB camera 125*b*. In that case, a face image of the user may be captured using the 3-D depth camera 125*a*, the detail information of the face image may be captured using the RGB camera 125*b*. Then, the controller 160 may process the detail information of the face image to obtain the user image information.

Figure 8A:
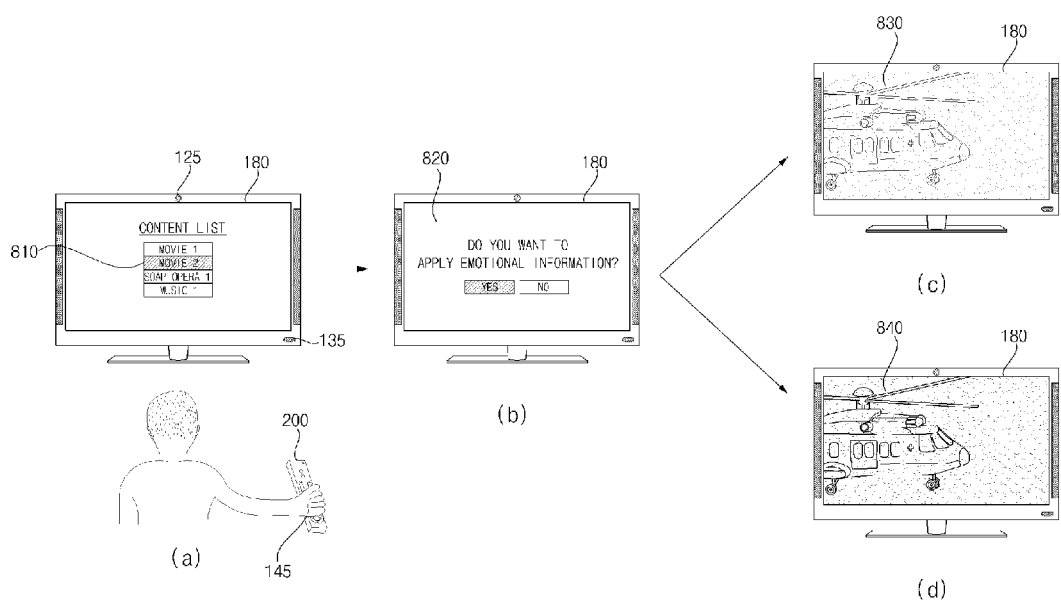
FIGS. 8 to 23 are views referred to for describing the digital data reproducing apparatus for reproducing content according to emotional information according to the embodiment of the present invention.

FIG. 8A illustrates an operation for changing the visual tone of reproduced content. Referring to FIG. 8A(a), upon the user selection of Movie 2 in a content list 810 using the remote controller 200, the controller 160 may obtain a captured image, recorded voice or a sensed body signal through the image capture unit 125, the voice recorder 135 or the body signal sensor 145 to determine the current emotional state of the user. Referring to FIG. 8A(b), the digital data reproducing apparatus 100 may display an object 820 asking whether to apply the emotional information to the content on the display 180, before the content is reproduced.

For instance, if the user is happy, the content takes on a relatively bright visual tone on a screen 830 as illustrated in FIG. 8A(c). On the other hand, if the user is sad, the content takes on a relatively dark visual tone on a screen 840 as illustrated in FIG. 8A(d). In addition, to help relieve user's sadness, the screen 830 having a bright visual tone may be applied as illustrated in FIG. 8A(c).

As stated before, the reproduction condition of the reproduced content may be adjusted based on the emotional state previously stored for the content, disregarding the current emotional state of the user. Specifically, if a Movie 2 elicits a feeling of sadness from the user in the past, the emotional state of the user regarding Movie 2 is set as sadness. Thereafter, when the user reproduces the Movie 2, the Movie 2 may be played back in a dark visual tone as illustrated in FIG. 8A(d).

Further, the content list 810 includes movies, dramas and music, as well as text content such as documents, e-books, etc., and the above operation may be applied to the text content.

Figure 8B:
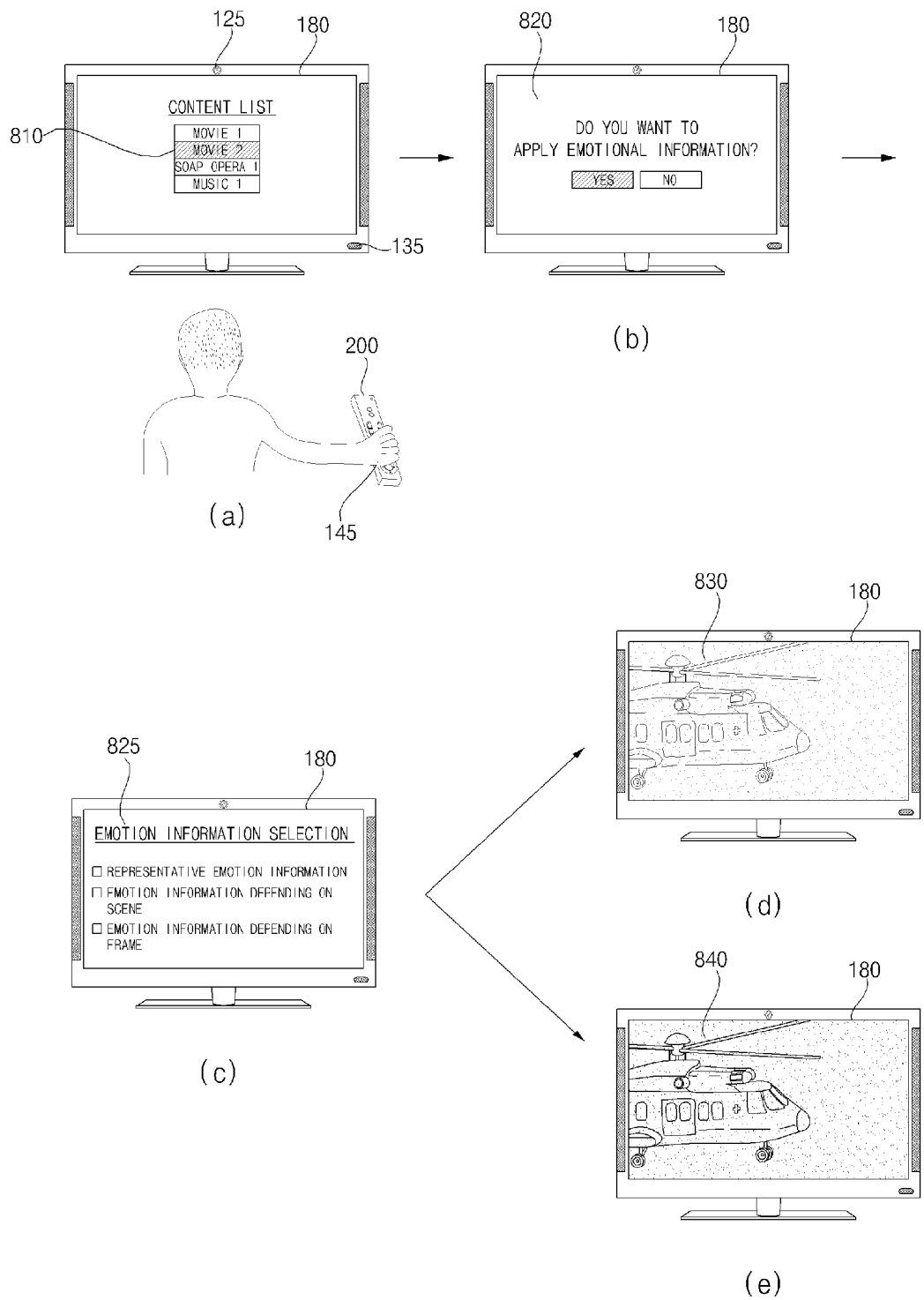

The operation illustrated in FIG. 8B is similar to the operation illustrated in FIG. 8A, except that the emotion information selection menu 825 is displayed in the display 180, before the content is reproduced. The emotion information can be stored as a representative emotion information (e.g., default), or an emotion information depending on each scene or frame, or an emotion information based on a time period.

Referring to FIG. 8B, the emotion information selection menu 825 may include 'representative emotion information' item, 'emotion information depending on scene' item, and 'emotion information depending on frame' item. Thus, user can select which kind of emotion information can be used in reproducing the content.

Figure 9:
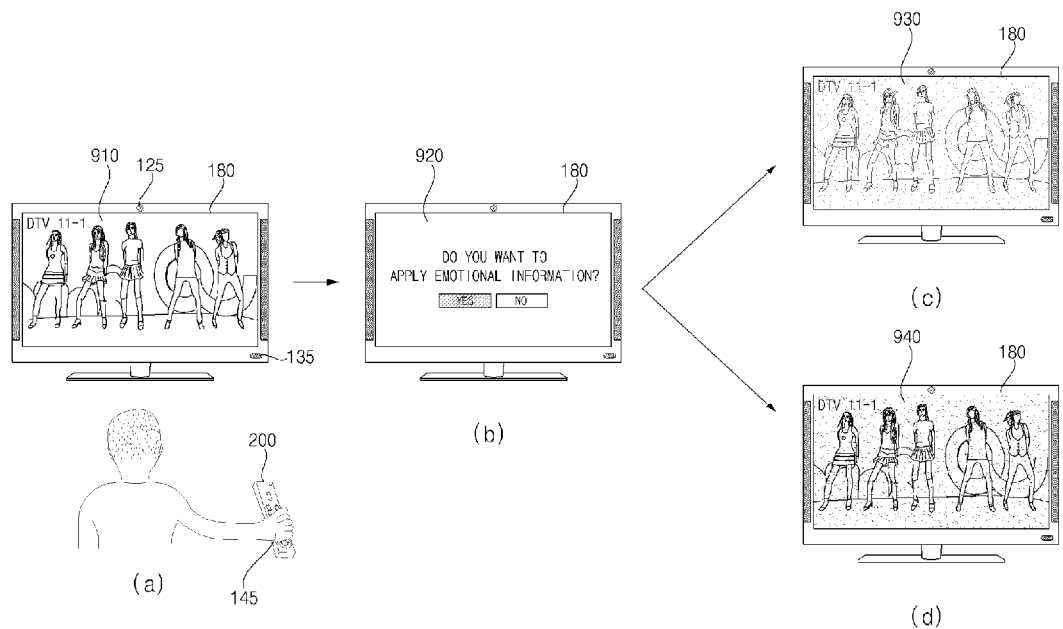

The operation illustrated in FIG. 9 is similar to the operation illustrated in FIG. 8A, except that the reproduced content is a broadcast signal of a channel, for example, channel DTV 11-1 received in real time, not pre-stored content. Referring to FIG. 9, when reproducing a broadcast signal in real time, the digital data reproducing apparatus 100 may modify at least one of the brightness, color or contrast of a broadcast image according to the current emotional state of the user. For example, if the user is happy, the broadcast image takes on a relatively bright visual tone on a screen 930 as illustrated in FIG. 9(c). On the other hand, if the user is sad, the broadcast image takes on a relatively dark visual tone on a screen 940 as illustrated in FIG. 9(d). Further, to help relieve the user's sadness, the screen 930 having a bright visual tone may be applied as illustrated in FIG. 9(c). In this manner, a broadcast signal can be reproduced to match the emotional state of the user.

Figure 10:
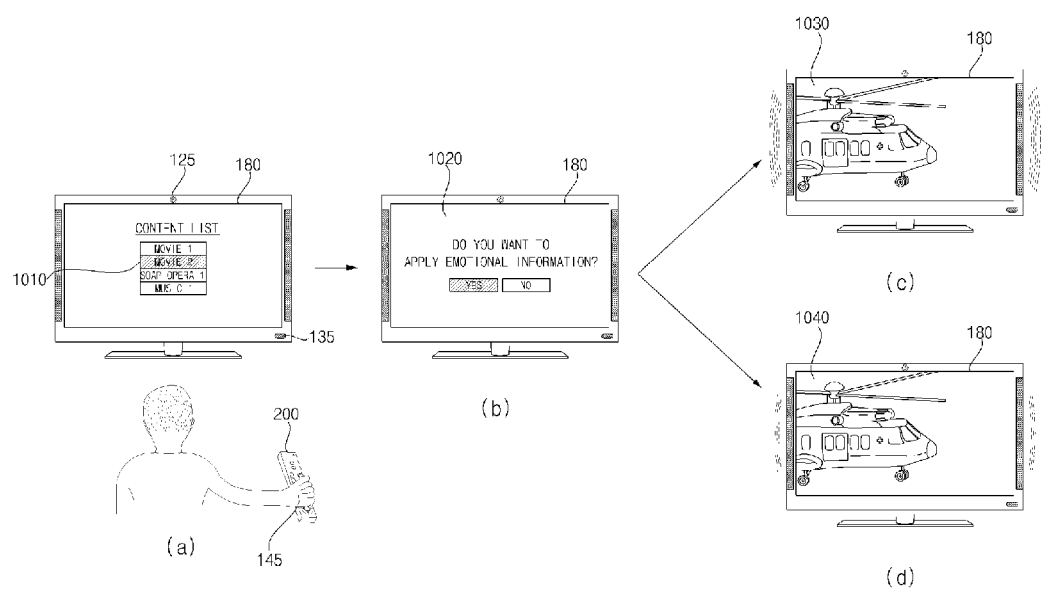

FIG. 10 illustrates an operation for changing the audio of reproduced content, such as sound volume, frequency, etc. Referring to FIG. 10, if the user is happy, the volume or frequency of the sound output from the audio output unit 185 may be increased as illustrated in FIG. 10(c). Additionally, a 3D effect may be reinforced. Meanwhile, if the user is sad, the volume or frequency of the sound output from the audio output unit 185 may be decreased as illustrated in FIG. 10(d).

FIG. 11 illustrates an operation for changing the ambient lighting of the digital data reproducing apparatus. Upon the user selection of the Movie 2 in a content list 1110 in FIG. 11(a), the digital data reproducing apparatus 100 may display an object 1120 asking whether to apply the emotional information to the content on the display 180 in FIG. 11(b). If the emotional information application mode is entered, the ambient lighting of the digital data reproducing apparatus 100 may be modified, in addition to the afore-mentioned image or audio adjustment, as illustrated in FIGS. 11(c) and 11(d). To adjust the ambient lighting, the digital data reproducing apparatus 100 may conduct a short-range communication with ambient lighting devices 1130 or 1140 in FIG. 11(c) or 11(d). The adjustment of ambient lighting enables a provision of a user-friendly service. Further, if the user is sad, the digital data reproducing apparatus 100 may control the volume up/down or the power up/down of a local electronic device through the short-range communication with the local electronic device.

Various examples of reproducing content according to emotional information will be described below with reference to FIGS. 12 to 20.

Referring to FIG. 12, with an image 1210 displayed on the display 180, the controller 160 may generate attention information of the user based on at least one of the user's motion, the viewing duration of the reproduced content, the sound volume, or the length of time the user fixes his or her gaze on the content. The user's motion and the length of the time the user fixes his or her gaze on the content may be obtained from an image of the user captured by the image capture unit 125. Referring to FIG. 12(a), when the user does not pay attention to the content, for example, when the user dozes off, the controller 160 determines that the attention of the user is low. Then, the controller 160 may decrease the brightness or volume of the reproduced content, or may turn off the digital data reproducing apparatus 100. As shown in FIG. 12(b), when the controller 160 determines that the user is dozing off, the brightness of an image 1220 is reduced from the original brightness set for the content. On the other hand, if the controller 160 determines that the attention of the user is high, it may increase the brightness or volume of the reproduced content, or may enlarge an image of the content. Further, when a plurality of users is present, the reproduction condition of the content may be adjusted based on the attention information in the similar manner.

Figure 13:
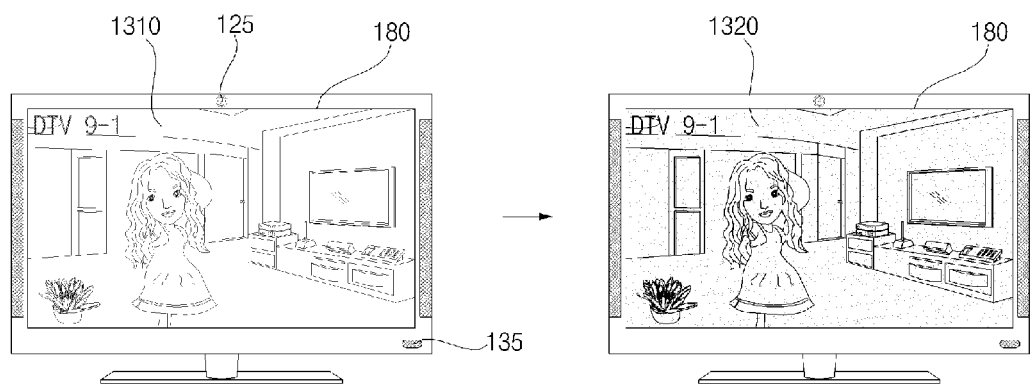
Figure 13:
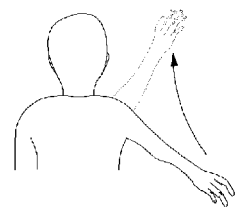
Figure 14:
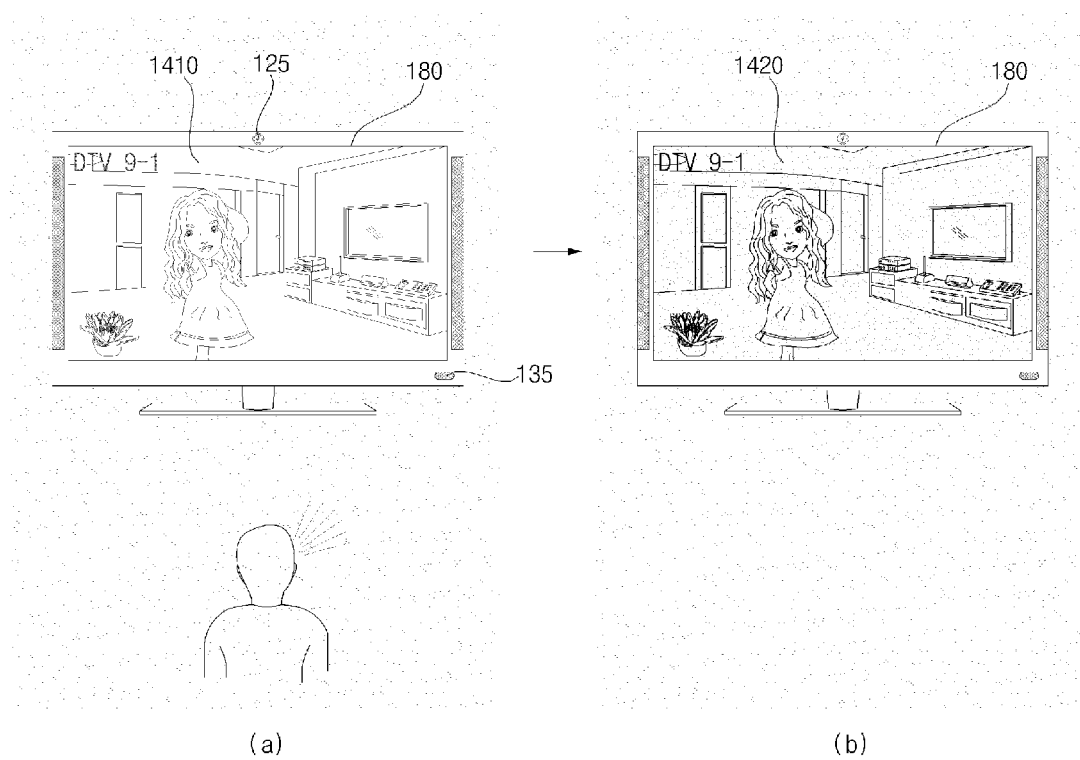

Referring to FIG. 13, with an image 1310 displayed on the display 180, the controller 160 may further generate emotional intensity information based on at least one of image information, voice information or physical information of the user. For example, a loud voice (e.g. voice with increased volume or intensity), a body movement, bushing, clapping hands, covering eyes with hands, or crying may be interpreted as an intense display of emotion. Alternatively, the emotional intensity may be correlated to the relative distances between facial feature points. If the relative distances between the facial feature points become smaller or larger than when the user is expressionless, it can be inferred that the user is emotionally intense.

FIG. 13(a) illustrates an embodiment of the present invention when the user feels an intense emotion. For example, if the user moves his or her arms or legs while viewing the image 1310, it can be inferred that the image 1310 is eliciting a strong emotional response from the user, that is, a stronger emotional response than if the user remains still. Therefore, the controller 160 may increase or decrease the brightness or sound volume of the reproduced content. FIG. 13(b) illustrates an image 1320 with a decreased brightness in response to the strong response detected from the user regarding the reproduce content. Further, in accordance with an embodiment of the present invention, the content may be reproduced according to the generated emotional information in real time while reproducing the content or according to the retrieved pre-stored emotional information such as in the form of metadata.

If the content is reproduced based on at least one of representative emotional information, attention information or emotional intensity information, a digital data reproducing apparatus manufacturer or the user may set the reproduction condition of the content. For example, if the content with the emotional state of the user is 'joy' is reproduced, the reproduction conditions of the content may be set to at least one of a luminance of +10, a brightness of +3, a volume of +5, a 3D depth of +2, or ambient lighting of +20 as a default by the manufacture or the user.

The reproduction conditions of the content may be further adjusted according to attention information or emotional intensity information. For example, if the emotional information and the attention information of the user are 'joy' and a Level 4, respectively, specific weights may be assigned to the reproduction conditions to reproduce the content accordingly. Further, if the emotional information and the emotional intensity information of the user are 'joy' and Level 3, respectively, specific weights may be assigned to the reproduction conditions to reproduce the content accordingly, different from the previous example.

The weights assigned according to the attention information and the emotional intensity information may be used in combination. For example, if the emotional information, the attention information, and the emotional intensity information of the user are 'joy', Level 3, and Level 4 respectively, the specific weights assigned to the reproduction conditions according to the attention information and the emotional intensity information may be combined to reproduce the content accordingly. When a plurality of users is present, the visual or audio adjustment of the reproduced content may be performed based on the emotional intensity information in the same manner.

Referring to FIG. 14, with an image 1410 displayed on the display 180, the controller 160 generates user's emotional information, taking into an account the ambient brightness of the digital data reproducing apparatus 100. Specifically, if the ambient lighting of the digital data reproducing apparatus 100 is low as illustrated in FIG. 14(a), the image information obtained from the image capture unit 125 may be inaccurate. Thus, emotional information may be generated, focusing on the voice or physical information of the user, rather than the image information of the user. Then, the controller 160 may increase the brightness or the volume of the reproduced content. FIG. 14(b) illustrates display of the image 1410 with decreased brightness.

Figure 15:
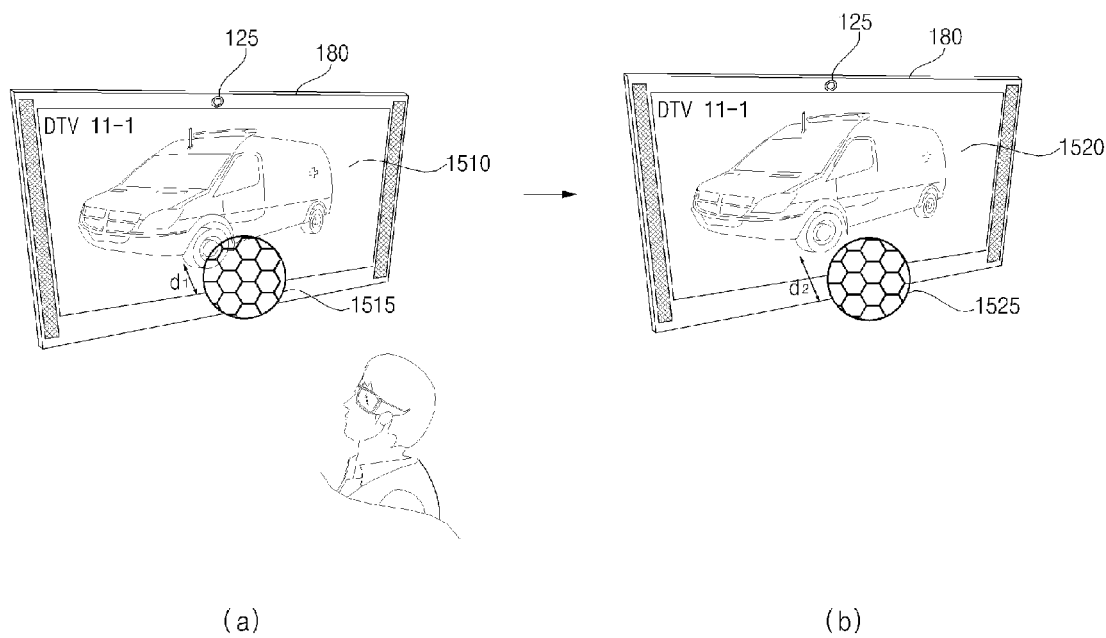

Referring to FIG. 15, with an image 1510 displayed on the display 180, the controller 160 may modify the depth of a 3D image according to user's emotional information. If the image 1510 is a 3D image containing a 3D object 1515 with a specific depth d1, the controller 160 generates emotional information of the user according to user's image information, voice information or physical information. Referring to FIG. 15(b), the depth of the 3D image is modified. For example, if the emotional state of the user is 'joy', a 3D image 1520 containing a 3D object 1525 with an increased depth d2 may be displayed on the display 180. On the other hand, if the emotional state of the user is 'sadness', the depth of the 3D image may be decreased. When a plurality of users is present, representative emotional information may be generated for the content based on attention information and emotional information of the individual users. Then, at least one of audio and video characteristics of the content may be modified based on the representative emotional information, when the content is reproduced. As stated before, the reproduction condition of the content may be adjusted, referring to representative attention information or representative emotional intensity information, in addition to the representative emotional information.

FIG. 16(a) illustrates an embodiment of the present invention when a plurality of users 1620 and 1630 views a broadcast image 1610. Representative emotional information of the users 1620 and 1630 may be generated using emotional information of each individual user.

When an object 1640 asks on the display 180 whether to reproduce the content according to user's emotional information and the user selects 'YES,' the digital data reproducing apparatus 100 enters into the emotional information application mode, as illustrated in FIG. 16(b). Referring to FIG. 16(c), at least one of the visual or audio of the reproduced content may be modified according to the generated or pre-stored representative emotional information of the users 1620 and 1630. In FIG. 16(c), an image 1650 with a reduced brightness is displayed, by way of an example. Further, the plurality of users 1620 and 1630 may watch the same broadcast image 1610 through different digital data reproducing apparatuses, not through the same digital data reproducing apparatus 100. Then, the digital data reproducing apparatuses may exchange the emotional information of the respective users with one another over the network. A specific one of the digital data reproducing apparatuses may collect the emotional information of the respective users and determine the representative emotional state of the users based on the collected emotional information.

Figure 17:
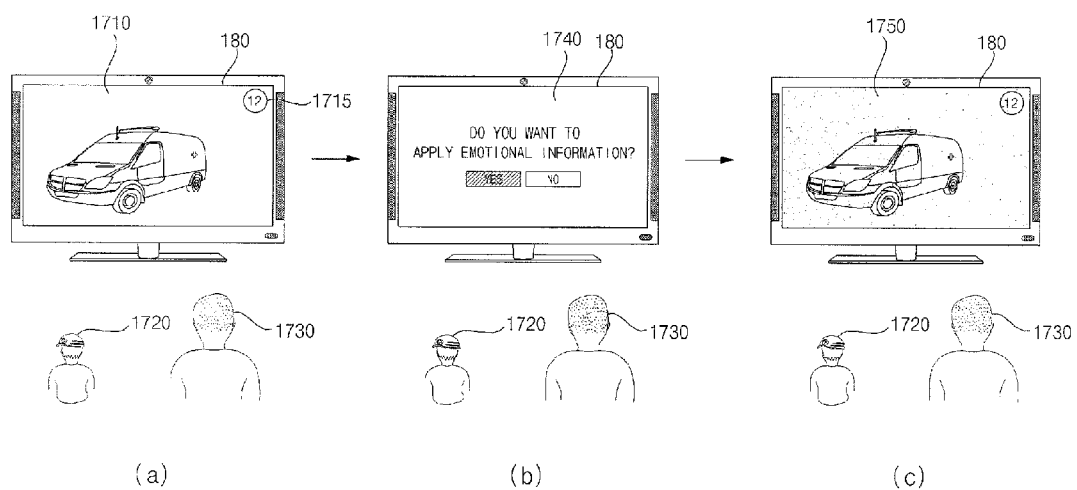

FIG. 17 illustrates an embodiment of the present invention when a plurality of users 1720 and 1730 views an image 1710. Depending on the category of the reproduced content, different weights may be assigned to the users 1720 and 1730. Further, the emotional information of the users 1720 and 1730 may be weighted with the different weights, and then, information about a representative emotion that the reproduced content elicits from the users 1720 and 1730 may be generated based on the weighted emotional information.

Referring to FIG. 17(a), an object 1715 indicating that the image 1710 is appropriate for children of the age 12 and under is displayed on the reproduced broadcast image 1710. When the users 1720 and 1730 are a child and an adult, respectively, representative emotional information of the child 1720 and the adult 1730 may be generated by assigning a higher weight to emotional information of the child 1720 than to emotional information of the adult 1730. Alternatively, the representative emotional information may be generated based on the emotional information of the child 1720 alone. Further, the content is restricted to audiences of the age 19 and above is displayed, the representative emotional information is created based on the emotional information of the adult 1730 alone. Upon a selection of the emotional information application mode through an object 1740 displayed on the display 180, asking whether to reproduce the content according to emotional information of a user, as illustrated in FIG. 17(b), the digital data reproducing apparatus 100 enters the emotional information application mode. Referring to FIG. 17(c), at least one of the visual or audio of the reproduced content may be modified according to the generated representative emotional information of the users 1720 and 1730. In FIG. 17(c), an image 1750 with a reduced brightness is displayed, by way of an example.

FIG. 18 illustrates displaying an object representing emotional information of the user. Referring to FIG. 18(a), an image 1810 is displayed on the display 180. Referring to FIG. 18(b), if newly generated or pre-stored emotional information of the user is 'joy', an image 1920 containing an object 1815 representing the emotional information of the user may be displayed on the display 180. The object 1815 may take the form of an icon, an avatar, etc. At least one of the visual or audio of the reproduced content may be modified according to the emotional information of the user. Referring to FIG. 18(*c*), an image 1830 having a decreased brightness is displayed on the display 180, for example.

FIG. 19 illustrates an operation for displaying an object representing the plurality of emotions when content elicits at least two emotions from a user. Referring to FIG. 19(*a*), with an image 1910 displayed on the display 180, emotional information of the user is determined. Referring to FIG. 19(*b*), if the user feels at least two emotions regarding the content, an object representing the plural emotions in an emotional information menu 1920 is displayed on the display 180. The emotional information menu 1920 may include three emotional information objects 1922, 1924 and 1926, each representing different emotions, having different sizes or colors. For instance, the second emotional information object 1924 representing 'joy' is displayed as the largest one according to the proportion of an emotion among the plurality of emotions. The plurality of emotional information objects 1922, 1924 and 1926 may be displayed in the form of numbers indicating the percentages of the respective emotions. In accordance with an embodiment of the present invention, representative emotional information for the specific content may be indicated as a value together with in a text or graphics. Accordingly, the user can determine whether to view the content or not, referring to the value of the representative emotion for the content, which is for example 70% or 85%. Upon the user's selection of one of the three emotional information objects 1922, 1924 and 1926, the visual or audio of the reproduced content may be modified according to the emotion information represented by the selected emotional information object. Referring to FIG. 19(*c*), the second emotional information object 1924 representing 'joy' is selected and thus an image 1930 with a reduced brightness is displayed, by way of an example.

FIG. 20 illustrates an operation of displaying an emotional information menu including emotional information, emotional intensity information or attention information. Referring to FIG. 20(*a*), with an image 2010 displayed on the display 180, pre-stored emotional information of a user is checked. Meanwhile, an object 2015 indicating the total run time of the content and an object 2018 indicating a current play position may further be displayed on the display 180. Referring to FIG. 20(*b*), if the user feels at least two emotions regarding the content, an object representing the plural emotions is displayed. In FIG. 20(*b*), an emotional information menu 2020 is displayed on the display 180. The emotional information menu 2020 may include three emotional information objects 2022, 2024 and 2026, each representing different emotions, having different sizes or colors, and emotional intensity objects 2023, 2025 and 2027 within the emotional information objects 2022, 2024 and 2026.

For instance, the second emotional information object 202 representing 'joy'4 is displayed as the largest one according to the proportion of an emotion among the plurality of emotions. Referring to FIG. 20(*b*), the size or value of the emotional intensity object 2025 for the second emotional information object 2024 is also larger than any other emotional intensity object 2023 or 2027. Thus, the second emotional information object 2024 and the emotional intensity object 2025 reveal that the 'joy' is the user's strongest emotion for the content. Upon the user's selection of one of the three emotional information objects 2022, 2024 and 2026 or one of the emotional intensity objects 2023, 2025 and 2027 within the selected emotional information object, the content may be reproduced, starting from a position corresponding to the emotional information represented by the selected emotional information object or the emotional intensity information represented by the selected emotional intensity object Referring to FIG. 20(*c*), a Level 4 from among Levels 1 to 4 of the emotional intensity object 2025 in the second emotional information object 2024 representing 'joy' is selected, and thus, an image 2030 of the content at a play position that pleases the user the most is displayed on the display 180. Therefore, a content part that elicits a desired emotion from the user can readily be reproduced.

Figure 21:
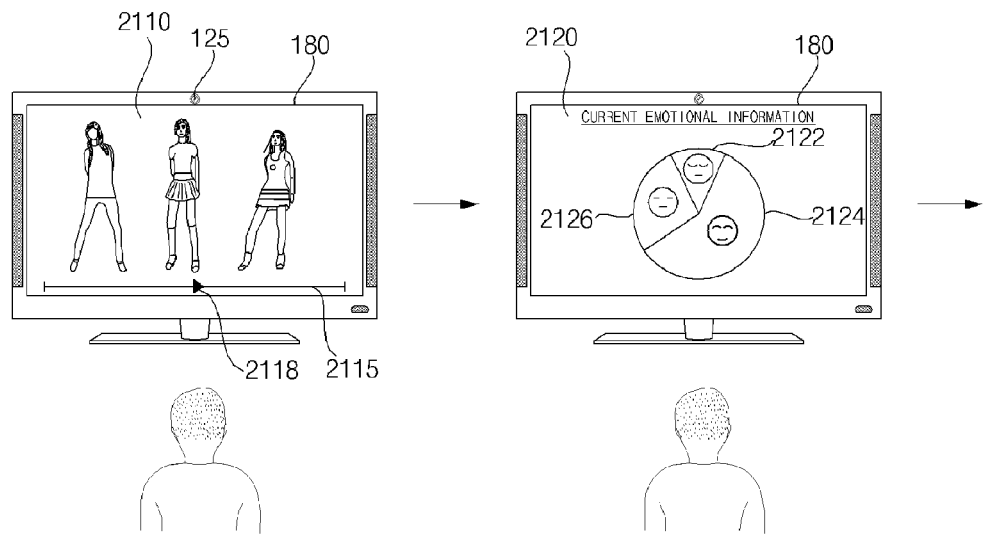
Figure 21:
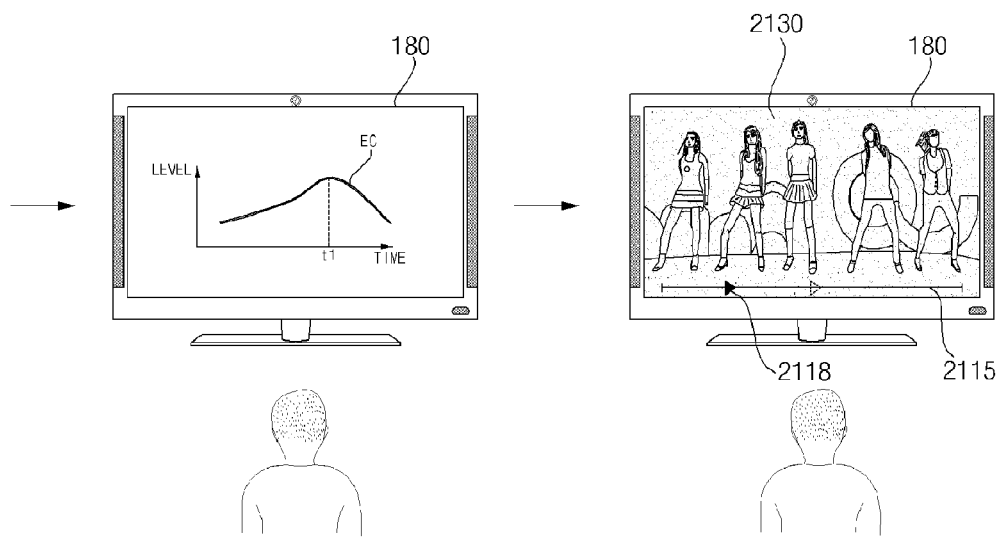

The operation illustrated in FIG. 21 is similar to the operation illustrated in FIG. 20, except that a user selects a specific emotional intensity level on an emotional curve (EC) representing emotional intensity levels over time. Referring to FIG. 21(*a*), with an image 2110 displayed on the display 180, pre-stored emotional information of the user is checked. Referring to FIG. 21(*b*), if the pre-stored emotional information represents at least two emotions for the content, an emotional information menu 2120 including a plurality of emotional information objects 2122, 2124 and 2126 is displayed on the display 2120. Referring to FIG. 21(*c*), upon a selection of the second emotional information object 2124 representing 'joy', the EC representing the intensity levels of 'joy' may be displayed on the display 180. As mentioned above, the EC may indicate intensity levels over time. Referring to FIG. 21(*d*), upon a selection of a specific time t1 on the EC, the content may be reproduced, starting from the time t1, that is, starting from a play position corresponding to the intensity level at time t1. Thus, an image 2130 of the reproduced content may be displayed. Meanwhile, an object 2115 indicating the total run time of the content and an object 2118 indicating a current play position may further be displayed on the display 180.

Figure 22:
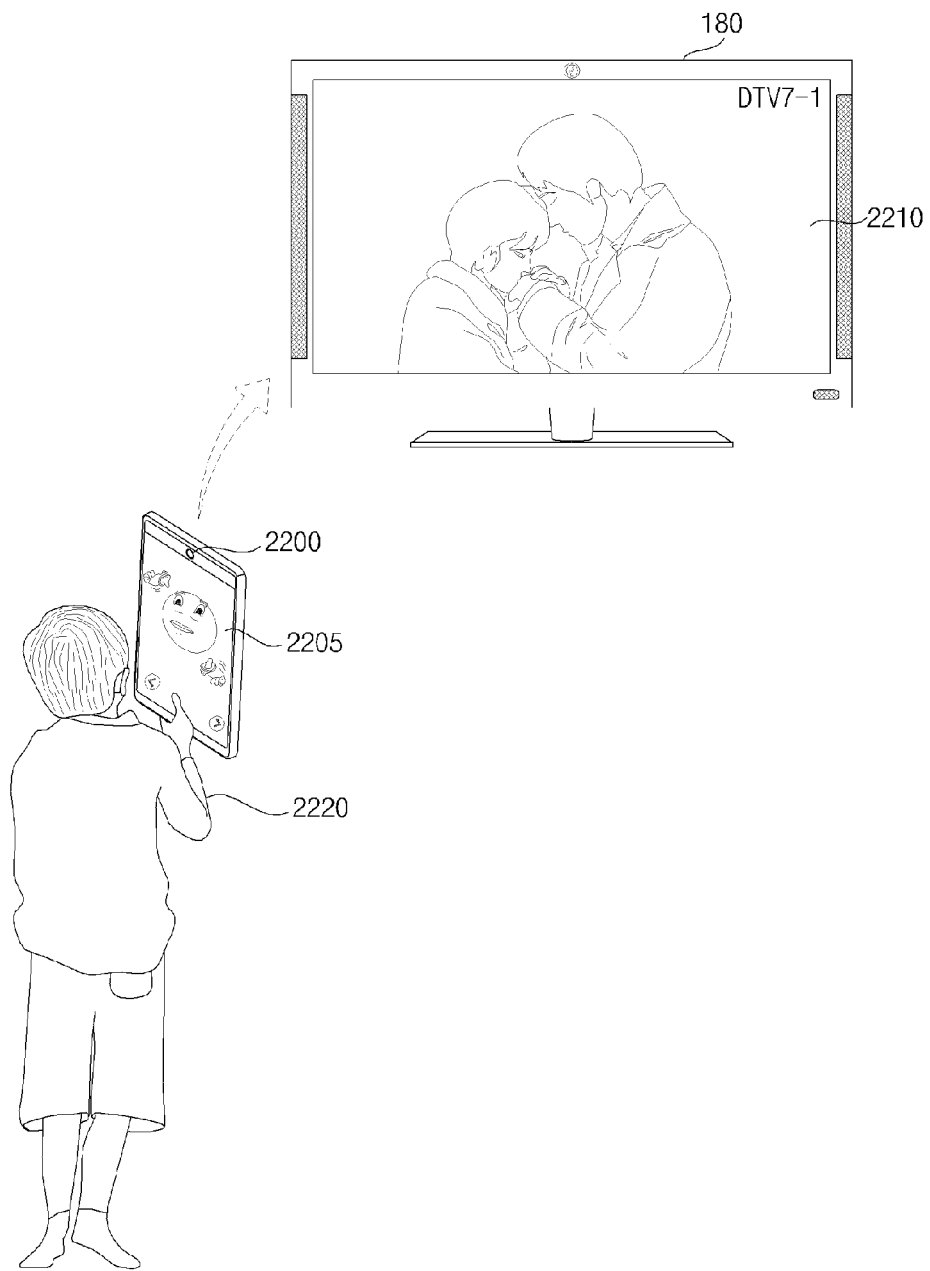

FIG. 22 illustrates an operation for transmitting user's emotion information about an image 2205 being reproduced on a portable terminal 2200 to the digital data reproducing apparatus 100, while a user 2220 is watching the image 2205 on the portable terminal 2200. Referring to FIG. 22, the digital data reproducing apparatus 100 may display a broadcast image 2210 and various settings can be applied for the broadcast image 2210 according to the transmitted user's emotional information. Meanwhile, the portable terminal 2200 may further transmit seamless reproduction information associated with a content displayed at the portable terminal 2200 in addition to emotion information associated with the content to the digital data reproducing apparatus 100. Then, the digital data reproducing apparatus 100 may modify at least one of audio and video characteristics of the content based on the emotion information, and seamlessly reproduce the content based on the seamless reproduction information and based on the modified at least one of audio and video characteristics of the content. The seamless reproduction information includes time stamp information associated with the content being displayed, when an event for requesting the seamless reproduction at the digital data reproducing apparatus occurs.

Figure 23:
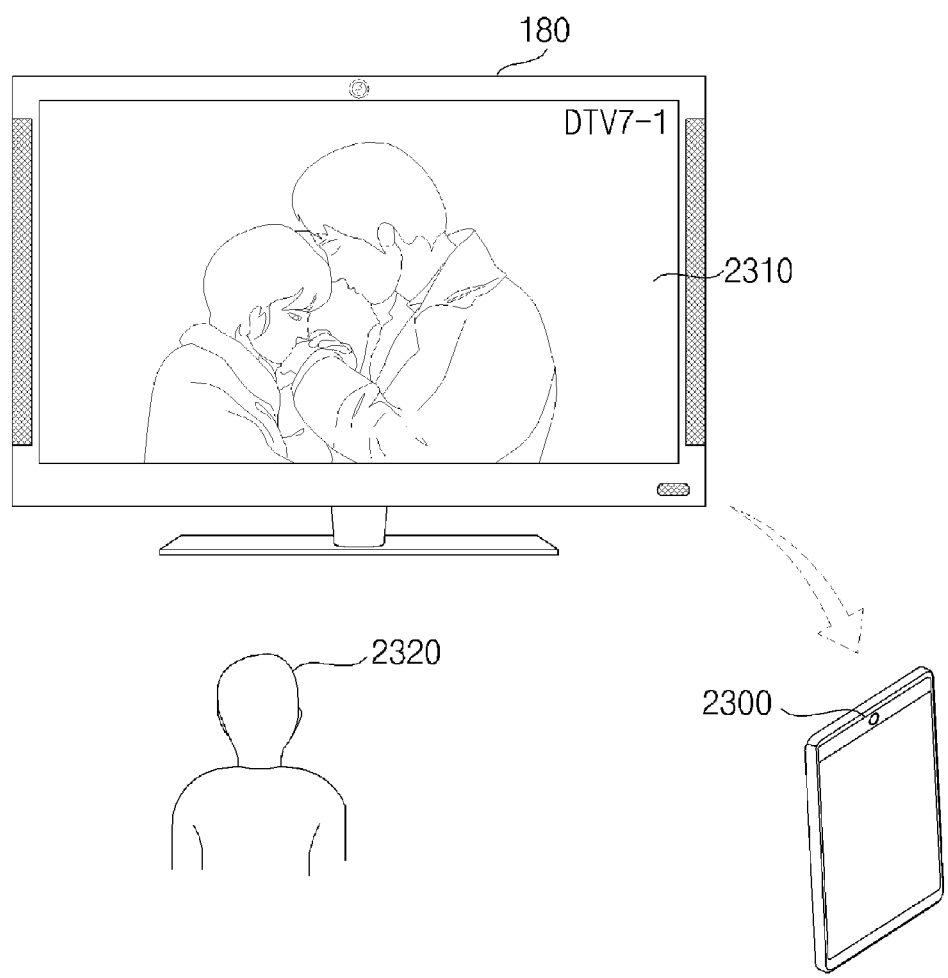

FIG. 23 illustrates an opposite case to FIG. 22, in which a user 2320 wirelessly transmits his or her emotional information concerning a broadcast image 2310 displayed on the digital data reproducing apparatus to a portable terminal 2300. The portable terminal 2300 may then reproduce the content later, referring to the received user's emotional information of the content. In addition, various settings can be used for displaying other contents on the portable terminal 2300 according to the transmitted user's emotional information. Meanwhile, the digital data reproducing apparatus may further transmit seamless reproduction information associated with the content displayed at the digital data reproducing apparatus 100 in addition to the emotion information associated with the content to the portable terminal 2300. Then, the portable terminal 2300 may modify at least one of audio and video characteristics of the content based on the emotion information, and seamlessly reproduce the content based on the seamless reproduction information and based on the modified at least one of audio and video characteristics of the content.

As is apparent from the above description of embodiments of the present invention, at least one of the visual or audio of reproduced content can be modified according to emotional information of a user. Accordingly, a customized content reproduction service can be provided according to the emotional state of the user.

According to the emotional state of the user, the ambient lighting of a digital data reproducing apparatus can also be modified. In addition, various user-friendly services can be provided. Since highly reliable emotional information is generated based on at least one of a captured user's image, recorded user's voice, or a body signal sensed from the user, user friendliness is further enhanced. In addition, the generated emotional information can be transmitted to another electronic device or a network server through a network interface unit so as to be utilized for general purposes.

The digital data reproducing apparatus and a method for controlling the same according to the foregoing embodiments are not restricted to the embodiments set forth herein. Therefore, variations and combinations of the embodiments set forth herein may fall within the scope of the present invention.

The method for controlling the digital data reproducing apparatus according to the foregoing embodiments may be implemented as code that can be written on a computer-readable recording medium and thus read by a processor. The computer-readable recording medium may be any type of recording device in which data is stored in a computer-readable manner. Examples of the computer-readable recording medium include a ROM, a RAM, a CD-ROM, a magnetic tape, a floppy disc, an optical data storage and a carrier wave (e.g., data transmission over the Internet). The computer-readable recording medium can be distributed over a plurality of computer systems connected to a network so that computer-readable code is written thereto and executed therefrom in a decentralized manner. Programs, code and code segments to realize the embodiments herein can easily be realized by one of ordinary skill in the art.

While the present invention has been particularly shown and described with reference to embodiments thereof, it will be understood by those of ordinary skill in the art that various changes in form and details may be made therein without departing from the spirit and scope of the present invention as defined by the following claims.

What is claimed is:

1. A method for controlling a digital data reproducing apparatus, the method comprising:
    obtaining, by the digital data reproducing apparatus, emotional information associated with at least one of a user and a content;
    displaying an object indicating whether to reproduce a content according to the emotional information;
    entering into an emotional information application mode based on a user's selection;
    modifying at least one of audio and video characteristics of the content for reproduction based on at least the emotional information, wherein the modifying step includes modifying a depth of a 3D content according to the emotional information; and
    reproducing the content based on the modified at least one of audio and video characteristics of the content; and
    exchanging the emotional information with other users watching the same content over a network;
    wherein obtaining emotional information further includes:
        capturing an image of at least a part of a user's body;
        recording the user's voice;
        sensing, via a body signal sensing unit in a remote control unit, physical attributes of the users to generate physical information of the user; and
        determining the emotional information of the user based on at least two of the captured image, the recorded voice, or the sensed body signal.

2. The method of claim 1, wherein the captured image, the recorded voice and the body signal are assigned different weights thereby obtaining the user's emotional information.

3. The method of claim 1, further comprising:
    generating an icon or avatar representing emotional information of the user; and
    displaying the icon or avatar together with the content.

4. The method of claim 1, wherein obtaining the emotional information further includes at least two of the following:
    obtaining representative emotional information associated with at least one of the user and the content;
    obtaining emotional information for each scene or frame of the content; or
    obtaining emotional information for each time period associated with the content.

5. The method of claim 4, further comprising:
    receiving the user's selection of the emotional information among the at least two of the representative information, the information for each scene or frame, and the emotional information for each time period,
    wherein the modifying step modifies the at least one of audio and video characteristics of the content based on the user-selected information.

6. The method of claim 1, further comprising:
    displaying an object indicating total run time of the content and an object indicating a current play position;
    displaying objects representing at least two pieces of obtained emotional information, respectively, when at least two pieces of emotional information are obtained;
    selecting one piece of emotional information according to a user's selection; and
    moving from a position in the content corresponding to the selected piece of emotional information and reproducing the content from the position,
    wherein each object representing different emotional information has a different size or color.

7. The method of claim 1, further comprising:
    obtaining, by the digital data reproducing apparatus, at least one of attentiveness information of the user and emotional intensity information associated with at least one of the user and the content,
    wherein the modifying step modifies the at least one of audio and video characteristics of the content based on the emotional information and based on at least one of the attentiveness information and the emotional intensity information.

8. The method of claim 1, further comprising:
    modifying an ambient lighting for the digital data reproducing apparatus based on the emotional information.

9. The method of claim 1, wherein the capturing step includes obtaining, by the digital data reproducing apparatus, user image information of a user using at least two cameras, the at two cameras including a 3-D depth camera and an RGB camera.

10. The method of claim 1, further comprising:
receiving, by the digital data reproducing apparatus from a transmitting apparatus, (a) seamless reproduction information associated with a content displayed at the transmitting apparatus, and (b) emotional information associated with the content; and
seamlessly reproducing, by the digital data reproducing apparatus, the content based on the seamless reproduction information and based on the modified at least one of audio and video characteristics of the content.

11. The method of claim 10, wherein the seamless reproduction information includes time stamp information associated with the content being displayed, when an event for requesting the seamless reproduction at the digital data reproducing apparatus occurs.

12. The method of claim 1, further comprising:
collecting emotional information of the respective users watching the same content; and
determining the representative emotional state of the users for the same content based on the collected emotional information.

13. The method of claim 1, further comprising:
displaying objects representing at least two pieces of emotional information, respectively, when at least two pieces of emotional information are obtained; and
selecting one piece of emotional information according to a user's selection,
wherein the modifying step modifies at least one of audio and video characteristics of the content based on the selected emotional information,
wherein each object representing different emotional information has a different size or color.

14. A digital data reproducing apparatus, comprising:
an image capturing unit configured to capture a video of a user to generate user image information;
an audio recording unit configured to record audio data of the user to generate voice information of the user;
a body signal sensing unit in a remote control unit, and configured to sense physical attributes of the user to generate physical information of the user;
a network interface unit configured to exchange data with another electronic device or an external network server;
at least one of a display unit and an audio output unit; and
a controller configured to:
obtain emotional information associated with at least one of the user and a content;
display an object indicating whether to reproduce a content according to the emotional information;
enter into an emotional information application mode based on a user's selection;
modify at least one of audio and video characteristics of a content for reproduction based on at least the emotional information;
reproduce the content, using the at least one of the display unit and the audio output unit, based on the modified at least one of audio and video characteristics of the content; and
determine the emotional information of the user based on at least two of the captured image, the recorded voice, and the sensed body signal;
wherein the controller controls the network interface unit to exchange the emotional information with other users watching the same content over a network; and wherein the controller modifies a depth of a 3D content according to the emotional information, when modifying the video characteristics of the content.

15. The apparatus of claim 14, wherein the captured image, the recorded voice and the body signal are assigned different weights thereby obtaining the user's emotional information.

16. The apparatus of claim 14, wherein the controller generates an icon or avatar representing emotional information of the user, and controls the display to display the icon or avatar together with the content.

17. The apparatus of claim 14, wherein the controller is further configured to obtain at least two of the following:
representative emotional information associated with at least one of the user and the content;
emotional information for each scene or frame of the content; or
emotional information for each time period associated with the content.

18. The apparatus of claim 17, wherein the controller is further configured to receive a user's selection among the at least two of the representative emotional information, the emotional information for each scene or frame, and emotional information for each time period, and to modify the at least one of audio and video characteristics of the content based on the user-selected emotion information.

19. The apparatus of claim 14, wherein the controller controls the display unit to display an object indicating total run time of the content and an object indicating a current play position and the controller displays objects representing the at least two pieces of emotional information, respectively, when at least two pieces of emotion information are obtained;
wherein the controller selects one emotion information according to a user's selection, and moves from a position in the content corresponding to the selected emotion and reproduces the content from the position; and
wherein each object representing different emotional information has a different size or color.

20. The apparatus of claim 14, wherein the controller is further configured to obtain at least one of attentiveness information of the user and emotional intensity information associated with at least one of the user and the content, and to modify the at least one of the audio and video characteristics of the content based on the emotional information and based on the attentiveness information and the emotional intensity information.

21. The apparatus of claim 14, wherein the controller is further configured to modify ambient lighting for the digital data reproducing apparatus based on the emotional information.

22. The apparatus of claim 15, wherein the controller collects the emotional information of the respective users watching the same content, and determines the representative emotional state of the users for the same content based on the collected emotional information.

23. The apparatus of claim 14, wherein the controller controls the display unit to display objects representing at least two pieces of emotional information, respectively, when at least two pieces of emotional information are obtained, selects one piece of emotional information according to a user's selection, and modifies at least one of audio and video characteristics of the content based on the selected emotional information; and
wherein each object representing different emotional information has a different size or color.

* * * * *